US008568727B2

(12) United States Patent
Adolf et al.

(10) Patent No.: US 8,568,727 B2
(45) Date of Patent: Oct. 29, 2013

(54) ANTIBODY MOLECULES SPECIFIC FOR FIBROBLAST ACTIVATION PROTEIN AND IMMUNOCONJUGATES CONTAINING THEM

(75) Inventors: Guenther Adolf, Vienna (AT); Elinborg Ostermann, Vienna (AT); Milena Kalat, Vienna (AT); Karl-Heinz Heider, Stockerau (AT)

(73) Assignee: Boehringer Ingelheim International GmbH, Igelheim am Rhein (DE)

( * ) Notice: Subject to any disclaimer, the term of this patent is extended or adjusted under 35 U.S.C. 154(b) by 760 days.

(21) Appl. No.: 12/159,070

(22) PCT Filed: Dec. 22, 2006

(86) PCT No.: PCT/EP2006/070185
§ 371 (c)(1),
(2), (4) Date: Nov. 14, 2008

(87) PCT Pub. No.: WO2007/077173
PCT Pub. Date: Jul. 12, 2007

(65) Prior Publication Data
US 2009/0304718 A1    Dec. 10, 2009

(30) Foreign Application Priority Data
Jan. 5, 2006 (EP) .................................. 06100121

(51) Int. Cl.
*A61K 39/395* (2006.01)
*C07K 1/107* (2006.01)
*C07K 16/00* (2006.01)

(52) U.S. Cl.
USPC ................ 424/178.1; 530/387.3; 530/388.24; 530/391.7; 530/402

(58) Field of Classification Search
USPC ............ 424/178.1; 530/387.3, 388.24, 391.7, 530/402
See application file for complete search history.

(56) References Cited

U.S. PATENT DOCUMENTS

| 2004/0241174 A1 | 12/2004 | Amphlett et al. |
| 2005/0123536 A1 | 6/2005 | Law et al. |

FOREIGN PATENT DOCUMENTS

| EP | 0953639 A1 | 11/1999 |
| EP | 1258255 A1 | 11/2002 |
| WO | 9957151 A2 | 11/1999 |
| WO | 0168708 A2 | 9/2001 |
| WO | 02083171 | 10/2002 |
| WO | 2005060999 A2 | 7/2005 |
| WO | 2005071073 A1 | 8/2005 |
| WO | 2005081711 A2 | 9/2005 |
| WO | 2005112619 A2 | 12/2005 |
| WO | 2005117986 A2 | 12/2005 |

OTHER PUBLICATIONS

Mersmann et al. (Int. J. Can. 92(2):240-248 (2001).*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Brocks, Bodo et al., "Species-Crossreactive scFv Against the Tumor Stroma Marker "Fibroblast Activation Protein" Selected by Phage Display from an Immunized FAP -/- Knock Out Mouse"; Molecular Medicine (2001) vol. 7, No. 7 pp. 461-469.
Ewert, Stefan et al.,"Stability Improvement of Antibodies for Extracellular and Intracellular applications: CDR Grafting to Stable Frameworks and Structure-Based Framework Engineering"; Methods (2004) vol. 34 pp. 184-199.
Hofheinz, R.D. et al., "Stromal Antigen Targeting by a Humanised Monoclonal Antibody: An Early Phase II Trial of Sibrotuzumab in Patients with Metastatic Colorectal Cancer"; Onkologie (2003) vol. 26 pp. 44-48.
International Search Report and Written Opinion for PCT/EP2006/070185 filed Dec. 22, 2006. Applicant: Boehringer Ingelheim International GmbH. Mailed Apr. 27, 2007.
Mersmann, Michael et el., "Human Antibody Derivatives Against the Fibroblast Activation Protein for Tumor Stroma Targeting of Carcinomas"; Int. Journal of Cancer (2001) vol. 92 pp. 240-248.
Strand, Vibeke et al., "Effects of Administration of an Anti-CD5 Plus Immunoconjugate in Rheumatoid Arthritis"; Arthritis and Rheumatism (1993) vol. 36, No. 5 pp. 620-630.
Welt, Sidney et al., "Antibody Targeting in Metastatic Colon Cancer: A Phase I Study of Monoclonal Antibody F19 Against a Cell-Surface Protein of Reactive Tumor Stromal Fibroblasts"; Journal Clinical Oncology (1994) vol. 12 pp. 1193-1203.
WO0168708 (Part 1 of 2) International Publication Date: Sep. 20, 2001. Applicant: Boehringer Ingelheim Pharma KG. Inventor: John-Edward Park. Title: Human FAP-µ-Specific Antibodies. Total pp. 236. Part 1 of 2. This foreign patent is too large for EFS submission via the Foreign patent section. Therefore filing in two parts in the NPL section. pp. 1-118.
WO0168708 (Part 2 of 2) International Publication Date: Sep. 20, 2001. Applicant: Boehringer Ingelheim Pharma KG. Inventor: John-Edward Park. Title: Human FAP-µ-Specific Antibodies. Total pp. 236. Part 2 of 2. This foreign patent is too large for EFS submission via the Foreign patent section. Therefore filing in two parts in the NPL section. pp. 119-236.
WO2005071073 (Part 1 of 2) International Publication Date: Aug. 4, 2005. Applicant: Point Therapeutics. Inventor: Paul A. Mclean. Title: FAP Compositions And The Use Thereof For Immunomodulation. Total pp. 178. Part 1 of 2. This foreign patent is too large for EFS submission via the Foreign patent section. Therefore filing in two parts in the NPL section. pp. 1-90.

(Continued)

*Primary Examiner* — Lynn Bristol
(74) *Attorney, Agent, or Firm* — Michael P. Morris; Edouard G. Lebel

(57) ABSTRACT

Anti-FAP-antibodies and immunoconjugates, pharmaceutical compositions containing such conjugates, and their use in cancer therapy.

15 Claims, 10 Drawing Sheets

(56) References Cited

OTHER PUBLICATIONS

WO2005071073 (Part 2 of 2) International Publication Date: Aug. 4, 2005. Applicant: Point Therapeutics. Inventor: Paul A. Mclean. Title: FAP Compositions And The Use Thereof For Immunomodulation. Total pp. 178. Part 2 of 2. This foreign patent is too large for EFS submission via the Foreign patent section. Therefore filing in two parts in the NPL section. pp. 91-178.

Schmidt, Alexej et al. "Generation of human high-affinity antibodies specific for the fibroblast activation protein by guided selection" European Journal of Biochemistry vol. 268 pp. 1730-1738 (2001).

WO1999057151(Part 1 of 2) International Publication Date: Nov. 11, 1999. Applicant: Boehringer Ingelheim International GmbH. Inventor: John-Edward Park. Title: FAP-µ-Specific Antibody with Improved Producibility. Total pp. 190. Part 1 of 2. This foreign patent is too large for EFS submission via the Foreign patent section. Therefore filing in two parts in the NPL section. pp. 1-95.

WO1999057151(Part 2 of 2) International Publication Date: Nov. 11, 1999. Applicant: Boehringer Ingelheim International GmbH. Inventor: John-Edward Park. Title: FAP-µ-Specific Antibody with Improved Producibility. Total pp. 190. Part 2 of 2. This foreign patent is too large for EFS submission via the Foreign patent section. Therefore filing in two parts in the NPL section. pp. 95-190.

WO2005081711 (Part 1 of 2) International Publication Date: Sep. 9, 2005. Applicant: Seattle Genetics Inc. Inventor: Svetlana O. Doronina. Title: Monomethylvaline Compounds Capable of Conjunction to Ligands. Total pp. 426. Part 1 of 2. This foreign patent is too large for EFS submission via the Foreign patent section. Therefore filing in two parts in the NPL section. pp. 1-200.

WO2005081711 (Part 2 of 2) International Publication Date: Sep. 9, 2005. Applicant: Seattle Genetics Inc. Inventor: Svetlana O. Doronina. Title: Monomethylvaline Compounds Capable of Conjunction to Ligands. Total pp. 426. Part 2 of 2. This foreign patent is too large for EFS submission via the Foreign patent section. Therefore filing in two parts in the NL section. pp. 201-426.

WO2005112619 (Part 1 of 2) International Publication Date: Dec. 1, 2005. Applicant: Genentech Inc. Inventor: Jane Brennan. Title: Novel Gene Disruptions, Compositions and Methods Relating Thereto. Total pp. 316. Part 1 of 2. This foreign patent is too large for EFS submission via the Foreign patent section. Therefore filing in two parts in the NPL section. pp. 1-150.

WO2005112619 (Part 2 of 2) International Publication Date: Dec. 1, 2005. Applicant: Genentech Inc. Inventor: Jane Brennan. Title: Novel Gene Disruptions, Compositions and Methods Relating Thereto. Total pp. 316. Part 2 of 2. This foreign patent is too large for EFS submission via the Foreign patent section. Therefore filing in two parts in the NPL section. pp. 151-316.

\* cited by examiner

ANTIBODY MOLECULES SPECIFIC FOR FIBROBLAST ACTIVATION PROTEIN AND IMMUNOCONJUGATES CONTAINING THEM

This application is a national phase entry under 35 U.S.C. 271 of international application PCT/EP2006/070185, filed Dec. 22, 2006, which claims priority to European Application No. EP 06 100 121.0, filed Jan. 5, 2006, each of which is hereby incorporated by reference in its entirety.

The invention relates to novel anti-FAP-α antibody molecules and cytotoxic immunoconjugates consisting of such antibody and a cytotoxic agent, e.g. a maytansinoid, pharmaceutical compositions comprising such immunoconjugates, and their use in tumour therapy.

There have been numerous attempts to improve the efficacy of antineoplastic drugs by conjugating such drugs to antibodies against tumour-associated antigens in order to elevate local concentration of the drug by targeted delivery to the tumour. Many of these approaches have met limited success, and several reasons have been discussed in the literature to explain the failure. For anticancer drugs acting stoichometrically, like e.g. doxorubicin or methotrexate, relatively high intracellular concentrations are necessary to exert the required cytotoxicity. These concentrations are thought to be difficult to achieve with many antibody-drug conjugates because of (a) insufficient potency of many common anticancer drugs, (b) low cell surface concentration of antigen targets, (c) inefficient internalization of antigen-antibody complexes into the target cell, and (d) inefficient release of free drug from the conjugate inside the target cell (Chari et al., 1992).

Two of the aforementioned drawbacks, namely (a) and (d), were addressed by the work of Chari and coworkers (Chari et al., 1992; Liu et al., 1996; U.S. Pat. No. 5,208,020). These authors developed antibody conjugates wherein the antibody is linked to a maytansinoid via a disulfide linkage. Maytansines belong to the class of Ansa macrolide antibiotics, which derive from *Nocardia* sp. The maytansine ansamitocin P-3, produced by bacterial fermentation, is used as a precursor molecule to manufacture maytansinoid DM1. Maytansine and derivatives act as anti-mitotic agents (inhibitors of tubulin polymerization), similar as vincristine, but with markedly higher potency than vincristine or other established chemotherapeutic agents (DM1 is toxic to cells in vitro at ~$10^{-10}$ M concentration). In contrast to the high cytotoxicity of free maytansinoid, the antibody conjugate has a toxicity which is several orders of magnitude lower on antigen-negative cells compared to antigen-positive cells. The linkage by disulfide bonding has the advantage that these bonds are readily cleaved inside the target cells by intracellular glutathione, releasing highly toxic free drug. This approach has been applied to antibodies against tumour-associated antigens, for example the C242-DM1 conjugate (Liu et al., 1996; Lambert et al., 1998), and HuN901-DM1 (Chari et al., 2000). However, the application of these conjugates is restricted due to the limited expression of the respective target antigens. For example, the antigen recognized by N901 (CD56, N-CAM) is predominantly expressed by tumours of neuroendocrine origin, the expression of the C242 antigen (CanAg) is mostly limited to tumours derived from the GI tract.

To improve this approach by applying it to suitable tumour-associated antigens with favorable antigen expression pattern, high and specific cell surface antigen concentration within the target tissue, and an efficient internalization process that transports the antigen complexed-antibody conjugate into the cells, anti-CD44-antibody-DM1 immunoconjugates were developed (WO 02/094325).

Nevertheless, there is still a need for innovative immunotherapeutics that have an inhibitory effect on tumour-associated target antigens having low expression in normal tissue and high expression in a great variety of tumours.

Immunohistochemical analyses have shown that Fibroblast Activation Protein (in the following, also termed "FAP") displays restricted distribution in normal tissue. Among non-neoplastic adult lesional tissues, expression of FAP has been observed in the activated fibroblasts of healing wounds, in rheumatoid arthritis, and in activated hepatic stellate cells during cirrhosis, whereas in normal adult tissue only pancreatic islet (A) cells are FAP positive. In contrast, FAP-positive stromal fibroblasts are seen in the stroma of over 90% of malignant breast, ovarian, colorectal, lung, skin, prostate and pancreatic tumours. A proportion of bone and soft tissue sarcoma tumour cells are also FAP positive (Rettig et al., 1988). Due to its broad expression in many common cancers and its restricted expression pattern in normal tissues, fibroblast activation protein alpha (FAP-α; in the following referred to as FAP) has been considered to be an attractive antigenic target, however, immunotherapies based on targeting the FAP antigen have not been successful.

The invasive growth of epithelial cancers is associated with a number of characteristic cellular and molecular changes in the supporting stroma. A highly consistent molecular trait of the reactive stroma of many types of epithelial cancer is induction of FAP, a cell surface molecule of reactive stromal fibroblasts (Garin-Chesa et al., 1990). Since the FAP antigen is selectively expressed in the stroma of a range of epithelial carcinomas, independent of location and histological type, the concept to target stroma by targeting FAP has been developed for imaging, diagnosis and treatment of epithelial cancers and certain other conditions. For this purpose, a monoclonal antibody termed F19 (secreted by the hybridoma cell line ATCC Accession No. HB 8269), that specifically binds to FAP was developed and described in U.S. Pat. No. 5,059,523 and WO 93/05804. To further improve this concept, the antibody F19 was humanized; the obtained antibody, that specifically binds to FAP, is described in WO 99/57151 (see below).

While selective accumulation of a murine anti-FAP MAb in tumour stroma tissue was demonstrated with trace-labeled ($^{131}$I-radiolabeled) murine monoclonal MAb F19 in biodistribution imaging studies (Welt, et al., 1994; Tanswell, et al., 2001), the concept of tumour inhibition by stroma targeting has not been successful in cancer therapy: While a phase I study $^{131}$I-radiolabeled anti-FAP MAb sibrotuzumab (BIBH1) demonstrated that administration of repeated infusions of sibrotuzumab is safe and well-tolerated (Scott et al., 2001; Hofheinz et al., 2003), in a phase II study with unlabeled sibrotuzumab that was carried out in patients with advanced metastatic colorectal cancer, ongoing tumour progression was noted in most patients. Therefore, since the minimum requirements were not met, this study was discontinued.

It was an objective of the invention to provide improved immunotherapeutics that are based on anti-FAP antibodies that target malignant tumour cells expressing the FAP antigen. It was a further objective of the invention to provide improved immunotherapeutics that are based on anti-FAP antibodies. Such immunotherapeutics should target FAP-expressing non-malignant stromal cells in tumours wherein the malignant cells do not express FAP, but nevertheless are efficiently killed by the immunotherapeutic drug.

For solving the problem underlying the invention, it was a prerequisite to first provide animal models suitable for proof-of-concept. The feasibility of animal experiments, which are crucial for proving the concept of targeting stromal cells and consequently—directly or indirectly—killing tumour cells, is based on the availability of an anti-FAP antibody that reacts with both human and mouse FAP.

Such cross-reactivity is a requirement for conducting studies in cancer models based on human tumour xenografts growing in immunodeficient mice, because in these models, while the tumour cells are of human origin, the stromal cells are derived from the mouse. The results of the experiments of the present invention have shown that anti-FAP antibodies conjugated to a highly cytotoxic maytansinoid very efficiently kill tumours in vivo. From the results of the experiments the inventors concluded that tumour killing may, on the one hand, be caused by targeting FAP to stromal cells due to its property of being a stromal antigen. On the other hand, it could be shown that the anti-FAP antibody maytansinoid conjugates are highly efficient in killing tumour cells in human tumour xenografts expressing FAP, an effect that could, in the chosen experimental setting, be ascribed to FAP's property of being a tumour antigen.

The present invention relates to novel anti-FAP antibody molecules and immunoconjugates consisting of any such FAP-specific antibody molecule conjugated to a maytansinoid.

In a first aspect, the present invention provides an anti-FAP-α antibody molecule selected from
a. a murine monoclonal antibody, defined by
   i. a variable heavy chain comprising the region from aa 20 to 136 of sequence (SEQ ID NO: 1);
   ii. a variable light chain comprising the region from aa 23 to 129 of sequence (SEQ ID NO:2) and
   iii. the IgG2a kappa subclass;
   or a fragment or derivative thereof,
b. a chimeric antibody derived from the murine monoclonal antibody defined in a);
c. a humanized antibody, derived from the murine monoclonal antibody defined in a); or a fragment or derivative thereof.

The monoclonal murine antibody defined in a) has been designated "MFP5".

In the following, the above-defined anti-FAP antibody molecules of the invention are termed "MFP5 antibodies" or "MFP5 antibody molecules".

It has been found that the antibody MFP5 reacts both with murine and human FAP. This provides a most advantageous feature of MFP5 antibody molecules/that also have this property, in that such MFP5 antibody molecules can be used to study the impact of stroma targeting, which is important for the therapeutic efficacy of the immunoconjugates of the invention. Since the tumor stroma in mouse xenograft models is of murine origin, this feature of crossreactivity is indispensable for conducting animal studies.

In an embodiment of the invention, the chimeric antibody b) is defined by
   i. a variable heavy chain comprising the region from aa 20 to 136 of sequence (SEQ ID NO: 1);
   ii. a variable light chain comprising the region from aa 23 to 129 of sequence (SEQ ID NO:2) and
   iii. constant heavy and light chains that are of human origin.

The construction and production of chimeric mouse/human antibodies, which represent the "first generation" of humanized antibodies, is well known in the art (Boulianne et al., 1984). The variable regions of the non-human antibody are typically linked to at least a portion of the immunoglobulin constant region ($F_c$) of a human immunoglobulin. Human constant region DNA sequences can be isolated in accordance with well-known procedures from a variety of human cells, preferably from immortalized B cells (see Kabat et al., 1991; supra, and WO 87/02671). The antibody molecules may contain all or only a portion of the constant region as long as they exhibit specific binding to the FAP antigen. The choice of the type and length of the constant region depends on whether effector functions like complement fixation or antibody dependent cellular toxicity are desired, and on the desired pharmacological properties of the antibody protein. The antibody molecule will typically be a tetramer consisting of two light chain/heavy chain pairs, but may also be dimeric, i.e. consisting of a light chain/heavy chain pair, e.g. a Fab or Fv fragment.

In yet another embodiment, the antibody is a chimeric FAP-specific antibody (designated cMFP5) that has the heavy chain variable region of MFP5 fused to the human heavy chain constant region (IgG1) (SEQ ID NO:3) and the light chain variable region of MFP5 fused to the human light chain constant region (kappa) (SEQ ID NO:4). In the experiments of the present invention, this antibody was expressed in mammalian cells and used for immunohistochemical staining of stromal cells in human tumour xenografts grown in nude mice.

Other human constant regions for chimerizing MFP5 are available to the person skilled in the art, e.g. IgG2, IgG3, IgG4, IgA, IgE or IgM and kappa or lambda light chain constant regions.

In an embodiment of the invention, the humanized antibody c) is defined by
   i. CDRs contained within the variable heavy chain that comprises the region from aa 20 to 136 of sequence (SEQ ID NO: 1) and by
   ii. CDRs contained within the variable light chain that comprises the region from aa 23 to 129 of sequence (SEQ ID NO:2)
   iii. frameworks supporting said CDRs that are from a human antibody,
   iv. constant heavy and light chains that are from a human antibody.

Humanized forms of non-human (e.g. murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (from the recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues.

In the humanized antibody defined in c), the complementarity determining regions (CDRs) of MFP5 have been grafted into the respective genes of human immunoglobulin heavy and light chains.

"Complementarity determining regions" (CDRs) of a monoclonal antibody are understood to be those amino acid sequences involved in specific antigen binding according Kabat et al. (1991), in connection with Chothia and Lesk (1987). From the sequences of the variable regions as contained in SEQ ID NO:1 and SEQ ID NO:2, the CDR sequence can be routinely determined by searching the Kabat sequence database for sequence features.

Appropriate framework residues of the CDR-grafted antibody may be reverted to murine residues to improve binding affinity. As described above, from methods pertinent to the art, the expert knows how to obtain the CDRs of MFP5, to choose and obtain appropriate human immunoglobulin genes, to graft the CDRs into these genes, to modify selected framework residues, to express the CDR-grafted antibody in appropriate host cells, e.g. Chinese hamster ovary (CHO) cells, and to test the resulting recombinant antibodies for binding affinity and specificity (see e.g. literature references above).

To obtain a humanized antibody, the antigen binding sites, which are formed by the CDRs of the heavy chain and CDRs of the light chain, are excised from the DNA of cells secreting the rodent (murine) monoclonal antibody and grafted into the DNA coding for the framework of the human antibody. Since only the antigen-binding site CDRs, rather than the entire variable domain of the rodent antibody, e.g. mouse antibody, are transplanted, the resulting humanized antibody ("second generation" antibody) is less immunogenic than a chimeric antibody.

In the experiments of the invention, two versions of a humanized antibody were obtained by CDR grafting. These antibodies show an affinity to FAP with $K_D$ of 30-40 nM, as determined by Surface Plasmon Resonance analysis.

Alternatively to CDR grafting, MFP5 can be humanized by the so-called "resurfacing" technology, whereby the murine frameworks are left unchanged with the exception of surface-exposed residues, as described in U.S. Pat. No. 5,639,641.

Nucleic acid molecules coding for the light chain and the heavy chain may be synthesised chemically and enzymatically (PCR amplification) by standard methods. First, suitable oligonucleotides can be synthesized with methods known in the art (e.g. Gait, 1984), which can be used to produce a synthetic gene. Methods to generate synthetic genes from oligonucleotides are known in the art (e.g. Stemmer et al., 1995; Ye et al., 1992; Hayden et Mandecki, 1988; Frank et al., 1987).

In yet another embodiment, the antibody is a MFP5 antibody, preferably a humanized antibody, recognizing an epitope within the FAP sequence that overlaps with the epitope recognized by MFP5. Overlapping epitopes can, for example, be determined by competitive binding. Competitive binding is determined in ELISA using plates coated with FAP protein or FAP peptides or with FAP positive cells (Cell ELISA) and measuring binding of biotinylated MFP5 antibody in presence of a competitor antibody. In the presence of a competing antibody or antibody-derived fragment, the binding of biotinylated MFP5 is reduced in the case that the antibodies recognise a shared epitope. To identify the MPF5 epitope peptide, fragments or short polypeptides or recombinant proteins derived from the FAP sequence can be synthesised or produced and the binding of MFP5 to said peptides/polypeptides measured in an ELISA assay. Peptides or protein fragments containing the epitope, or DNA molecules encoding such peptides/fragments, respectively, may be used for immunization to obtain antibodies reactive with the same epitope as MFP5.

The nucleic acid molecules encoding the antibody heavy and light chains may be cloned into an expression vector (either both chains in one vector molecule, or each chain into a separate vector molecule), which then is introduced into a host cell. Expression vectors suitable for immunoglobulin expression in prokaryotic or eukaryotic host cells and methods of introduction of vectors into host cells are well-known in the art. In general, the immunoglobulin gene therein is in functional connection with a suitable promoter, like for example a human cytomegalovirus (CMV) promoter, hamster ubiquitin promoter (WO 97/15664), or a simian virus SV40 promoter located upstream of the Ig gene. For termination of transcription, a suitable termination/polyadenylation site like that of the bovine growth hormone or SV40 may be employed. Furthermore, an enhancer sequence may be included, like the CMV or SV40 enhancer. Usually, the expression vector furthermore contains selection marker genes like the dihydrofolate reductase (DHFR), glutamine synthetase, adenosine deaminase, adenylate deaminase genes, or the neomycin, bleomycin, or puromycin resistance genes. A variety of expression vectors are commercially available from companies such as Stratagene, La Jolla, Calif.; Invitrogen, Carlsbad, Calif.; Promega, Madison, Wis. or BD Biosciences Clontech, Palo Alto, Calif. For example, expression vectors pAD-CMV1 (NCBI GenBank Accession No. A32111) or pAD-CMV19 (NCBI GenBank Accession No. A32110) may be used for expression. The host cell preferably is a mammalian host cell, e.g. a COS, CHO, or BHK cell, more preferably a chinese hamster ovary (CHO) cell, e.g. a CHO-DUKX (Urlaub and Chasin, 1980), CHO-DG44 (Urlaub et al., 1983), or CHO-K1 (ATCC CCL-61) cell. The host cell then is cultured in a suitable culture medium under conditions where the antibody is produced, and the antibody is then isolated from the culture according to standard procedures. Procedures for production of antibodies from recombinant DNA in host cells and respective expression vectors are well-known in the art (see e.g. WO 94/11523, WO 97/9351, EP 0 481 790, EP 0 669 986).

An example for a humanized anti-FAP antibody is BIBH1, which was used in some comparative experiments of the invention. It contains an amino acid sequence (variable region of the light chain) as in SEQ ID NO:2 of WO 99/57151, further contains an amino acid sequence (variable region of the heavy chain) as set forth in SEQ ID NO:12 of WO 99/57151 and further contains an amino acid sequence (constant region of the light chain) as set forth in SEQ ID NO:20 of WO 99/57151 and an amino acid sequence (constant region of the heavy chain) as set forth in SEQ ID NO:22 of WO 99/57151.

In a further aspect, the MFP5 antibody molecule is an MFP5 antibody fragment. To obtain antibody fragments, e.g. Fab fragments, digestion can be accomplished by means of routine techniques, e.g. using papain. Examples of papain digestion are described in WO 94/29348 and U.S. Pat. No. 4,342,566. Papain digestion of antibodies typically produces two identical antigen binding fragments, so-called Fab fragments, each with a single antigen binding site, and a residual Fc fragment. Pepsin treatment yields an F(ab')$_2$ fragment that has two antigen combining sites and is still capable of cross-linking the antigen.

The Fab fragments obtained by digestion of the antibody also contain the constant domains of the light chain and the first constant domain (CH$_1$) of the heavy chain. Fab' fragments differ from Fab fragments in that they contain additional residues at the carboxy terminus of the heavy chain CH$_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Antibody fragments can also be generated by molecular biology methods producing the respective coding DNA fragments.

The MFP5 antibody molecules may contain all or only a portion of the constant region as long as they exhibit specific binding to the relevant portion of the antigen. The choice of the type and length of the constant region depends on whether effector functions like complement fixation or antibody dependent cellular toxicity are desired, and on the desired pharmacological properties of the antibody protein. The antibody molecule will typically be a tetramer consisting of two light chain/heavy chain pairs, but may also be dimeric, i.e. consisting of a light chain/heavy chain pair, e.g. a Fab or Fv fragment, or it may be a monomeric single chain antibody (scFv; Johnson and Bird, 1991).

In another embodiment, the MFP5 antibody molecule may be a so-called "antibody-like molecule" (which is considered a derivative of an MFP5 antibody), which is a polypeptide containing short sequences or fragments of immunoglobulins. In particular, these are polypeptides containing one or more antigen binding regions that are identical or similar to a complementarity determining region (CDR) of an immunoglobulin. Such molecules can also be minibodies or single domain antibodies, e.g. so-called "nanobodies", which are micro-scaffolds comprising a CDR2 or CDR3 polypeptide sequence interconnecting fragments of the adjacent framework polypeptide sequences, which are arranged to form two anti-parallel-strands (described e.g. in WO 03/050531 and by Revets et al., 2005). Other examples for antibody-like molecules (or MFP5 antibody derivatives) are immunoglobulin super family antibodies (IgSF; Srinivasan 2005), camelized antibodies or other CDR containing or CDR grafted molecules or "Domain Antibody" (dAb). dABs are functional binding units of antibodies, corresponding to the variable regions of either the heavy (VH) or light (VL) chains of human antibodies. Domain Antibodies have a molecular weight of approximately 13 kDa, or less than one-tenth the size of a full antibody. A series of large and highly functional libraries of fully human VH and VL dAbs has been developed. dABs are also available for "dual targeting", i.e. dAbs that bind, in addition to FAP, to a second target in one molecule. dAb libraries, selection and screening methods, dAb formats for dual targeting and for conferring extended serum half life are described in e.g. U.S. Pat. No. 6,696,245, WO 04/058821, WO 04/003019 and WO 03/002609.

In general antibody fragments and derivatives (antibody-like molecules) are well expressed in bacterial, yeast, and mammalian cell systems.

Alternatively, the MFP5 antibody-like molecule may be a so-called "SMIP" ("Small Modular Immunopharmaceutical"). This molecule employs a single polypeptide chain as its binding domain Fv, which is linked to single-chain hinge and effector domains devoid of the constant domain CH1 (WO 02/056910). The molecules can be prepared as monomers or dimers, but they do not assume the dimer-of-dimers structure of traditional antibodies.

In a further aspect, the invention relates to an immunoconjugate of formula

A(LB)$_n$ (Formula (I))

wherein
A is an MFP5 antibody molecule, as defined above;
L is a linker moiety;
B a cytotoxic agent; and
n is a decimal number with n=1 to 10.

In the following, immunoconjugates containing an MFP5 antibody (molecule) are designated "MFP5 (immuno)conjugates".

Immunoconjugates containing the murine monoclonal antibody MFP5 have been shown to be effective in destroying various tumours associated with activated stromal fibroblasts; MPF5 conjugates are therefore useful for the therapy of such tumours. Alternatively, instead of using an MFP5 immunoconjugate, the MFP5 antibody (molecule) may be used as such, i.e. in non-conjugated form.

Compound B, which is toxic to cells, is a cytotoxic agent.

In accordance with the invention, the above-defined MFP5 antibody molecule is chemically coupled to any suitable cytotoxic agent, particularly a cytotoxic agent that induces cytotoxicity (e.g. apoptosis or mitotic arrest) of tumor cells, to form an immunoconjugate of the invention. As a result of normal pharmacologic clearance mechanisms, an antibody employed in a drug conjugate contacts and binds to target cells only in limited amounts. Therefore, the cytotoxic agent employed in the conjugate must be highly cytotoxic such that sufficient cell killing occurs to elicit a therapeutic effect. As described in US 2004/0241174, examples of such cytotoxic agents include taxanes (see, e.g. WO 01/38318 and WO 03/097625), DNA-alkylating agents (e.g., CC-1065 analogs), anthracyclines, tubulysin analogs, duocarmycin analogs, doxorubicin, auristatin E, and cytotoxic agents comprising a reactive polyethylene glycol moiety (see, e.g., Sasse et al. 2000; Suzawa et al., 2000; Ichimura et al., 1991; Francisco et al., 2003; U.S. Pat. Nos. 5,475,092, 6,340,701, 6,372,738, and 6,436,931, US 2001/0036923, US 2004/0001838, US 2003/0199519 and WO 01/49698).

In a preferred embodiment, the cytotoxic agent is a maytansinoid, i.e. a derivative of maytansine (CAS 35846538).

As described in US 2004/02241174, maytansinoids are known in the art to include maytansine, maytansinol, C-3 esters of maytansinol, and other maytansinol analogues and derivatives (see, e.g., U.S. Pat. Nos. 5,208,020 and 6,441, 163). C-3 esters of maytansinol can be naturally occurring or synthetically derived. Moreover, both naturally occurring and synthetic C-3 maytansinol esters can be classified as a C-3 ester with simple carboxylic acids, or a C-3 ester with derivatives of N-methyl-L-alanine, the latter being more cytotoxic than the former. Synthetic maytansinoid analogues also are known in the art and described in, for example, Kupchan et al., (1978). Methods for generating maytansinol and analogues and derivatives thereof are described in, for example, U.S. Pat. No. 4,151,042.

Suitable maytansinoids for use in the immunoconjugates of the invention can be isolated from natural sources, synthetically produced, or semi-synthetically produced using methods known in the art. Moreover, the maytansinoid can be modified in any suitable manner, so long as sufficient cytotoxicity is preserved in the ultimate conjugate molecule. In this regard, maytansinoids lack suitable functional groups to which antibodies can be linked. A linking moiety desirably is utilized to link the maytansinoid to the antibody to form the conjugate. The linking moiety contains a chemical bond that allows for the activation of maytansinoid cytotoxicity at a particular site. Suitable chemical bonds are well known in the art and include disulfide bonds, acid labile bonds, photolabile bonds, peptidase labile bonds, thioether bonds formed between sulfhydryl and maleimide groups, and esterase labile bonds. In a preferred embodiment, the linking moiety comprises a disulfide bond or a thioether bond. In accordance with the invention, the linking moiety preferably comprises a reactive chemical group. Particularly preferred reactive chemical groups are N-succinimidyl esters and N-sulfosuccinimidyl esters.

In a preferred embodiment, the reactive chemical group can be covalently bound to the maytansinoid via disulfide bonding between thiol groups. Thus, a maytansinoid modified as described herein preferably comprises a thiol group. One of ordinary skill in the art will appreciate that a thiol group contains a sulfur atom bonded to a hydrogen atom and is typically also referred to in the art as a sulfhydryl group, which can be denoted as "—SH" or "RSH."

Particularly preferred maytansinoids comprising a linking moiety that contains a reactive chemical group are C-3 esters of maytansinol and its analogs where the linking moiety contains a disulfide bond and the chemical reactive group comprises a N-succinimidyl or N-sulfosuccinimidyl ester. Many positions on maytansinoids can serve as the position to chemically link the linking moiety. For example, the C-3 position having a hydroxyl group, the C-14 position modified with hydroxymethyl, the C-15 position modified with hydroxy and the C-20 position having a hydroxy group are all useful. The linking moiety most preferably is linked to the C-3 position of maytansinol. Most preferably, the maytansinoid used in connection with the immunoconjugate of the invention is $N^{2'}$-deacetyl-$N^{2'}$-(-3-mercapto-1-oxopropyl)-maytansine (DM1) or $N^{2'}$-deacetyl-$N^{2'}$-(4-mercapto-4-methyl-1-oxopentyl)-maytansine (DM4).

Linking moieties with other chemical bonds also can be used in the context of the invention, as can other maytansinoids. Specific examples of other chemical bonds include acid labile bonds, thioether bonds, photolabile bonds, peptidase labile bonds and esterase labile bonds. Methods for producing maytansinoids with linking moieties are described in, for example, U.S. Pat. Nos. 5,208,020, 5,416,064, and 6,333,410.

The linking moiety of a maytansinoid typically and preferably is part of a larger linker molecule that is used to join the antibody to the maytansinoid. Any suitable linker molecule can be used in connection with the invention, as long as the linker molecule provides for retention of the cytotoxicity and targeting characteristics of the maytansinoid and the antibody, respectively. The linker molecule joins the maytansinoid to the antibody through chemical bonds (as described above), such that the maytansinoid and the antibody are chemically coupled (e.g. covalently bonded) to each other. Desirably, the linker molecule chemically couples the maytansinoid to the antibody through disulfide bonds or thioether bonds. Most preferably, the antibody is chemically coupled to the maytansinoid via disulfide bonds.

Particularly preferred linker molecules include, for example, N-succinimidyl 3-(2-pyridyldithio)propionate (SPDP) (see, e.g., Carlsson et al., (1978)), N-succinimidyl 4-(2-pyridyldithio)butanoate (SPDB) (see, e.g., U.S. Pat. No. 4,563,304), N-succinimidyl 4-(2-pyridyldithio)pentanoate (SPP) (see, e.g., CAS Registry number 341498-08-6), N-succinimidyl 4-(N-maleimidomethyl)cyclohexane-1-carboxylate (SMCC) (see, e.g., Yoshitake et al., *Eur. J. Biochem.*, 101, 395-399 (1979)), and N-succinimidyl 4-methyl-4-[2-(5-nitro-pyridyl)-dithio]pentanoate (SMNP) (see, e.g., U.S. Pat. No. 4,563,304). Preferred linker molecules for use in the conjugates of the invention are SPP, SMCC, and SPDB.

The choice of linker depends on the therapeutic situation—while administration of the conjugates with cleavable linkers has the benefits, in particular at lower dosages, of the so-called "bystander effect", i.e. the cytolytic effect of the toxin on surrounding cells that are not directly targeted by the antibody part of the immunoconjugates, the linker system containing an uncleavable linker (e.g. the thioester linker SMCC) offers the possibility of an antibody drug conjugate with lower toxicity and a larger therapeutic window.

By way of example, the MFP5 antibody maytansinoid conjugate of the invention may be prepared from a maytansinoid of formula Formula (II)

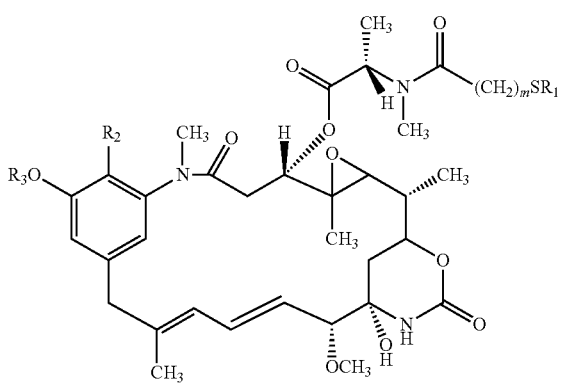

wherein
$R_1$ represents H or $SR_4$, wherein $R_4$ represents methyl, ethyl, linear alkyl, branched alkyl, cyclic alkyl, simple or substituted aryl, or heterocyclic;
$R_2$ represents Cl or H;
$R_3$ represents H or $CH_3$; and
m represents 1, 2, or 3.
Preferably, $R_1$ is H, $CH_3$, or $SCH_3$, $R_2$ is $C_1$, $R_3$ is $CH_3$, and m=2.
The maytansinoid with $R_1$=H, $R_2$=$C_1$, $R_3$=$CH_3$, and m=2 is designated DM1 in the literature.

In an embodiment, the immunoconjugate of the invention has the formula (Formula III)

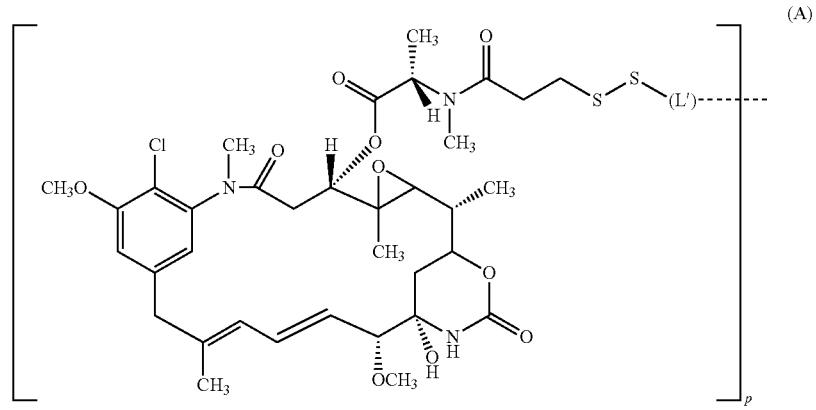

wherein

A is an MFP5 antibody molecule; as defined above, (L') is an optional linker moiety;

p is a decimal number with p=1 to 10.

Preferably, p is 2 to 4, more preferably about 2.5 to 3.5.

As mentioned above, methods for preparing such maytansinoids are known in the art (see in particular U.S. Pat. No. 5,208,020, Example 1); they have also been described in WO 02/094325 for generating an anti-CD44 antibody maytansinoid conjugate.

Conveniently, in a first step the maytansinoid C-3 ester ansamitocin P3 may be produced by bacterial fermentation of microorganisms belonging to the genus *Nocardia* or *Actinosynnema*, e.g. ATCC 31565, ATCC 31281 (U.S. Pat. No. 4,356,265; U.S. Pat. No. 4,450,234; WO 01/77360). Ansamitocin P3 may be extracted from the culture using organic solvents like ethyl acetate or toluene, and further purified by adsorption chromatography using e.g. silica gel. It may then be reduced to maytansinol using $LiAlH_4$ (U.S. Pat. No. 4,360,462) or, as suggested more recently, $LiAl(OMe)_3H$ or other LiAl or NaAl hydrids (WO 02/16368). The maytansinol may then be esterified at the C-3 position with N-methyl-L-alanine or N-methyl-L-cysteine derivatives to yield a disulfide-containing maytansinoid (U.S. Pat. Nos. 5,208,020; 5,416,064; 6,333,410), for example using dicyclohexylcarbodiimide (DCC) and catalytic amounts of zinc chloride (U.S. Pat. Nos. 4,137,230; 4,260,609). In a preferred embodiment, the maytansinol is esterified with the compound N-methyl-N-(3-methyldithiopropanoyl)-L-alanine of formula

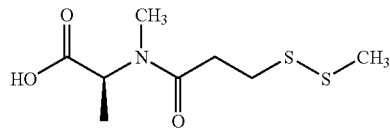

to yield the maytansinoid of Formula (II) with $R_1=SR_4$, $R_4=CH_3$, $R_2=Cl$, $R_3=CH_3$, and m=2.

The free thiol group may then be released by cleavage of the disulfide bond with dithiothreitol (DTT), to yield e.g. DM1.

The immunoconjugate of the invention can be formed using any method, e.g. using the methods described for generating the anti-CD44 maytansinoid conjugates (WO 02/094325). Upon intracellular cleavage, the free maytansinoid is released from the conjugate $A(LB)_n$. The free drug released from the immunoconjugate of the invention $A(LB)_n$ may have the formula B—X, wherein X is an atom or a chemical group, depending on the nature of the cleaving reaction. Preferably, X is a hydrogen atom, as for example when the linker moiety is just a covalent bond between two sulfur atoms, or a hydroxyl group. The cleavage site may also be within the linker moiety if the linker moiety is a chemical group, generating free drug of formula B-L"-X upon cleavage, wherein X is an atom or a chemical group, depending on the nature of the cleaving reaction. Preferably, X is a hydrogen atom or a hydroxyl group.

In a preferred embodiment, the immunoconjugate of formula (I) is less toxic than the toxic compound B, B—X or B-L"—X released upon intracellular cleavage. Methods of testing cytotoxicity in vitro are known in the art (Goldmacher et al., 1985; Goldmacher et al., 1986; see also U.S. Pat. No. 5,208,020, Example 2). Preferably, the immunoconjugate (I) is 10 times or more, more preferably 100 times or more, or even 1000 times or more less toxic than the free drug released upon cleavage.

Preferably, the MFP5 antibody molecule maytansinoid conjugates are those that are joined via a disulfide bond, as discussed above, that are capable of deliver maytansinoid molecules. Such cell binding conjugates are prepared by known methods such as modifying monoclonal antibodies with succinimidyl pyridyldithiopropionate (SPDP) or pentanoate (SPP) (Carlsson et al, 1978). The resulting thiopyridyl group is then displaced by treatment with thiol-containing maytansinoids to produce disulfide linked conjugates. Alternatively, in the case of the aryldithiomaytansinoids, the formation of the antibody conjugate is effected by direct displacement of the aryl-thiol of the maytansinoid by sulfhydryl groups previously introduced into antibody molecules. Conjugates containing 1 to 10 maytansinoid drugs linked via a disulfide bridge are readily prepared by either method. In this context, it is understood that the decimal number n in the formula $A(LB)_n$ is an average number as not all conjugate molecules of a given preparation may have the identical integer of LB residues attached to the antibody molecule.

The maytansinoid is preferably linked to the MFP5 antibody by a disulfide moiety and has the formula

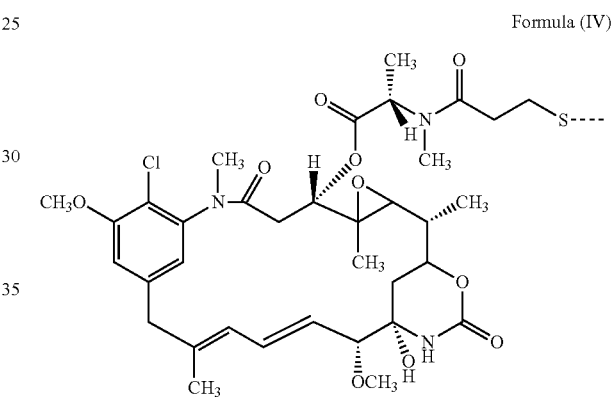

Formula (IV)

wherein the link to the antibody is through the sulfur atom shown in formula IV to a second sulfur atom present in the antibody molecule. To create such a sulfur atom available for bonding, an antibody molecule may be modified by introduction of a suitable linker as outlined above. Preferably, the maytansinoid is linked to the antibody molecule through a —S—$CH_2CH_2$—CO—, a —S—$CH_2CH_2CH_2CH_2$—CO—, or a —S—$CH(CH_3)CH_2CH_2$—CO— group. The sulfur atom in such a linker group forms the disulfide bond with the maytansinoid, while the carbonyl function may be bonded to an amino function present on the side chain of an amino acid residue of the antibody molecule.

That way, one or more maytansinoid residues may be linked to an antibody molecule. Preferably, 2 to 4 maytansinoid residues are linked to an antibody molecule.

In a further embodiment, the present invention relates to a method for producing an immunoconjugate of formula (I) comprising the steps:

(a) introducing free or protected thiol groups into an MFP5 antibody molecule;

(b) reacting the antibody molecule of step (a) with maytansinoid, and (c) recovering the resulting MFP5 immunoconjugate.

In a further embodiment, the present invention relates to a pharmaceutical composition comprising an MFP5 antibody molecule of the invention or an immunoconjugate of the invention of formula (I), preferably together with a pharmaceutically acceptable carrier, excipient, or diluent.

Suitable pharmaceutically acceptable carriers, diluents, and excipients are well known and can be determined by those of skill in the art as the clinical situation warrants. Examples of suitable carriers, diluents and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose. An example for a pharmaceutical composition useful for the immunoconjugate of the invention is described in US 2004/0241174.

The pharmaceutical compositions of the invention may be used for all kinds of clinical or non-clinical applications wherein a maytansinoid is to be targeted to cells expressing FAP, in particular to human tumour cells or human stromal fibroblasts.

The pharmaceutical compositions containing an antibody molecule and/or immunoconjugate of the invention and a pharmaceutically acceptable carrier are useful for treating tumour diseases that are associated with activated stromal fibroblasts and/or tumours that express FAP. In particular, the pharmaceutical composition of the invention is useful for the treatment of tumour diseases selected from the group consisting of colorectal cancers, non-small cell lung cancers, breast cancers, head and neck cancer, ovarian cancers, lung cancers, invasive bladder cancers, pancreatic cancers and metastatic cancers of the brain, head and neck squamous cell carcinoma (SCC), esophagus SCC, lung SCC, skin SCC, melanoma, breast adenocarcinoma (AC), lung AC, cervix SCC, pancreas AC, colon AC, or stomach AC, thyroid cancers, prostate cancer, osteosarcoma (OS) or soft tissue sarcoma. In addition benign tumours expressing FAP, e.g. desmoid tumours can be treated with the immunoconjugate of the invention.

In a further embodiment, the present invention relates to a method of treatment of cancer comprising applying a pharmaceutical composition as described before to a patient. In particular, this aspect of the invention relates to a method of treatment of cancer in a patient in need thereof, comprising administering to the patient a therapeutically effective amount of an immunoconjugate as described above, or a pharmaceutical composition as described above, for the cancer indications defined above.

For clinical treatment of cancer, the immunoconjugate of formula (I) according to the invention can be supplied in the form of a solution that is tested for sterility and for endotoxin levels. Examples of suitable protocols of immunoconjugate administration are as follows: Conjugates may be given weekly for 1 to 6 weeks either as an i.v. bolus, or as a continuous infusion for 5 days. Bolus doses can be given in 50 to 100 ml of normal saline to which 5 to 10 ml of human serum albumin has been added. Continuous infusions can be given in 250 to 500 ml of normal saline, to which 25 to 50 ml of human serum albumin has been added, per 24 hour period. Dosages will generally be 10 mg to 400 mg/m$^2$ of body surface area per application. The dose applied to the patient per administration has to be high enough to be effective, but must be below the dose limiting toxicity (DLT). In general, a sufficiently well tolerated dose below DLT will be considered maximum tolerated dose (MTD). The expert knows how to determine the MTD (Lambert et al., 1998). For weekly administrations, the MTD can be expected to be in the range of 100 to 200 mg/m$^2$. Alternatively, intervals between applications may be longer, e.g. two to four weeks, preferably three weeks. In this case, the MTD can be expected to be in the range of 200 to 300 mg/m$^2$. Alternatively, application may be in 5 daily doses, followed by a break of several weeks after which treatment may be repeated. In this case, the MTD per administration can be expected to be lower than 100 mg/m$^2$. For example, conjugates can be administered as a single i.v. infusion with a rate of 3 mg/min every 21 days. Up to 7 cycles of treatment were applied. It is to be understood that the applied doses may well be out of the ranges given above if the clinical situation requires. For example, if the MTD is found to be higher than indicated, single administration may be at a higher dose than 400 mg/m$^2$, or weekly may be at more than 200 mg/m$^2$. The amount of applied conjugate also depends on the type of linker; for cleavable linkers, as mentioned above, the higher bystander effect achieved by the released toxin may allow for lower dosages than when using a non-cleavable conjugate.

Dose, route of administration, application scheme, repetition and duration of treatment will in general depend on the nature of the disease (type, grade, and stage of the tumour etc.) and the patient (constitution, age, gender etc.), and will be determined by the medical expert responsible for the treatment. Besides treatment of solid tumours, therapeutic application according to the invention may be advantageous as an adjuvant to surgical intervention, to treat minimal residual disease.

The antibodies and immunoconjugates of the invention may also be used for the therapy of diseases in which expression of FAP is causally involved, e.g. for the therapy of rheumatoid arthritis.

In a further embodiment, the invention relates to the use of an antibody of the invention and/or an immunoconjugate of formula (I) for the preparation of a pharmaceutical composition for the treatment of cancer and rheumatoid arthritis.

EXAMPLE 1

Generating of Anti-FAP Antibody Maytansinoid Immunoconjugates 1.1. Generation of Antibodies
1.1.1. Anti-FAP Antibody BIBH1:

The humanized antibody BIBH1 (also designated sibrotuzumab), derived from the monoclonal antibody F19, is obtained as described in WO 99/57151. This antibody reacts with human FAP, but does not react with mouse FAP.

1.1.2. Anti-FAP Monoclonal Antibody MFP5:

The hybridoma cell line MFP5 secreting the murine monoclonal MFP5 is generated as described in WO 95/33771 for VFF18, except that FAP –/– knock out mice (Niedermeyer et al. 2000) strain C57BL/6 are used for immunisation due to the high homology of murine and human FAP. The antigen used for immunization is a CD8-murine FAP fusion protein (SEQ ID NO: 5; Niedermeyer 1998). Cross-reactivity of the secreted antibody MFP5 to human FAP is verified by using a cell ELISA assay (see Example 2) on the recombinant human fibrosarcoma cell line HT1080 (HT1080; ATCC CCL 121), clone v1.33, expressing human FAP (obtained by transfecting HT1080 cells with cDNA encoding human FAP. The results are shown in Example 2, FIG. 1.

The antibody is purified from cell culture supernatant on a protein A sepharose column.

1.1.3. Chimeric Antibody cMFP5:

mRNA is extracted from the hybridoma cell line MFP5 which secretes the antibody MFP5. In subsequent RT-PCR reactions, the variable light chain DNA and variable heavy chain DNA is amplified using specific primers homologous to the known leader sequences (forward primers) and to the constant region (backward primers) of murine heavy and light chain immunoglobulins (Jones and Bendig, 1991). The variable chain sequences are then cloned accordingly into a mammalian expression vector containing the human kappa light chain and the human IgG1 heavy chain constant region sequences. The chimeric MFP5 antibody is then expressed transiently in HEK 293 cells and purified on a protein A sepharose column.

1.2. Generation of Antibody-DM1 Conjugates:

The murine monoclonal antibody MFP5 and the humanised recombinant antibody BIBH1 are linked to the maytansinoid DM1 as described by Chari et al., 1992; Liu et al., 1996; U.S. Pat. No. 5,208,020. The conjugates are designated BIBH1-DM1 and MFP5-DM1, respectively. (In the following Examples, if not otherwise indicated, the designation "MFP5-DM1" stands for MFP5-SPP-DM1, i.e. the disulfide-linked immunoconjugate.

Fractions of antibody DM1 conjugate samples are assayed for the number of DM1 molecules linked per antibody molecule. (Linked DM1 molecules are determined by measuring the absorbance at both 252 nm and 280 nm). DM1/MAb ratio in the pooled solution is found to be 2.6-3.25 and the yield of conjugated antibody is at least 50% based on starting antibody.

EXAMPLE 2

Figure 1A:
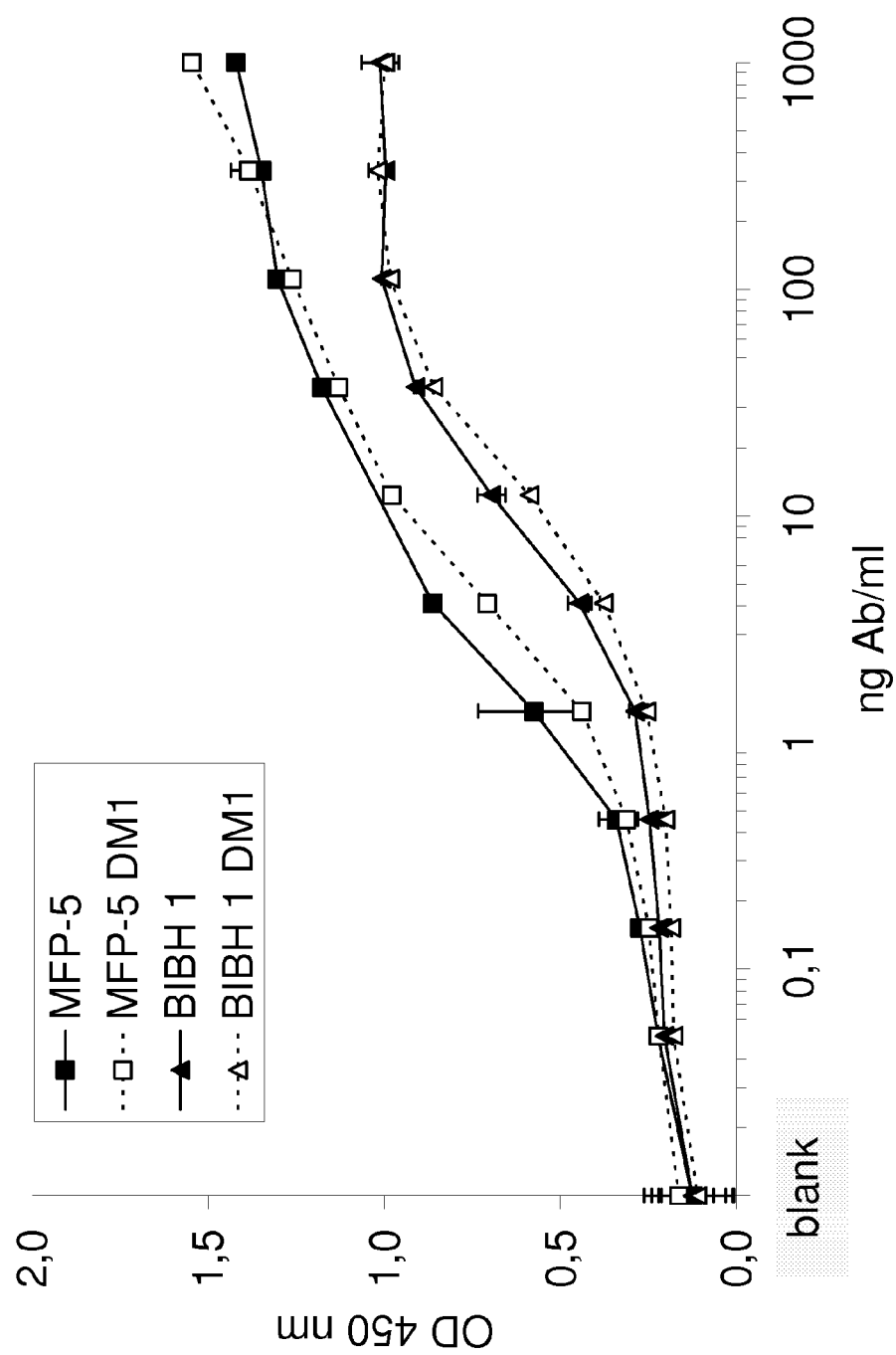
FIG. 1: Comparison of binding affinity of anti-FAP antibodies and their DM1 conjugates in Cell ELISA on FAP-positive fibrosarcoma cells.
Figure 1B:
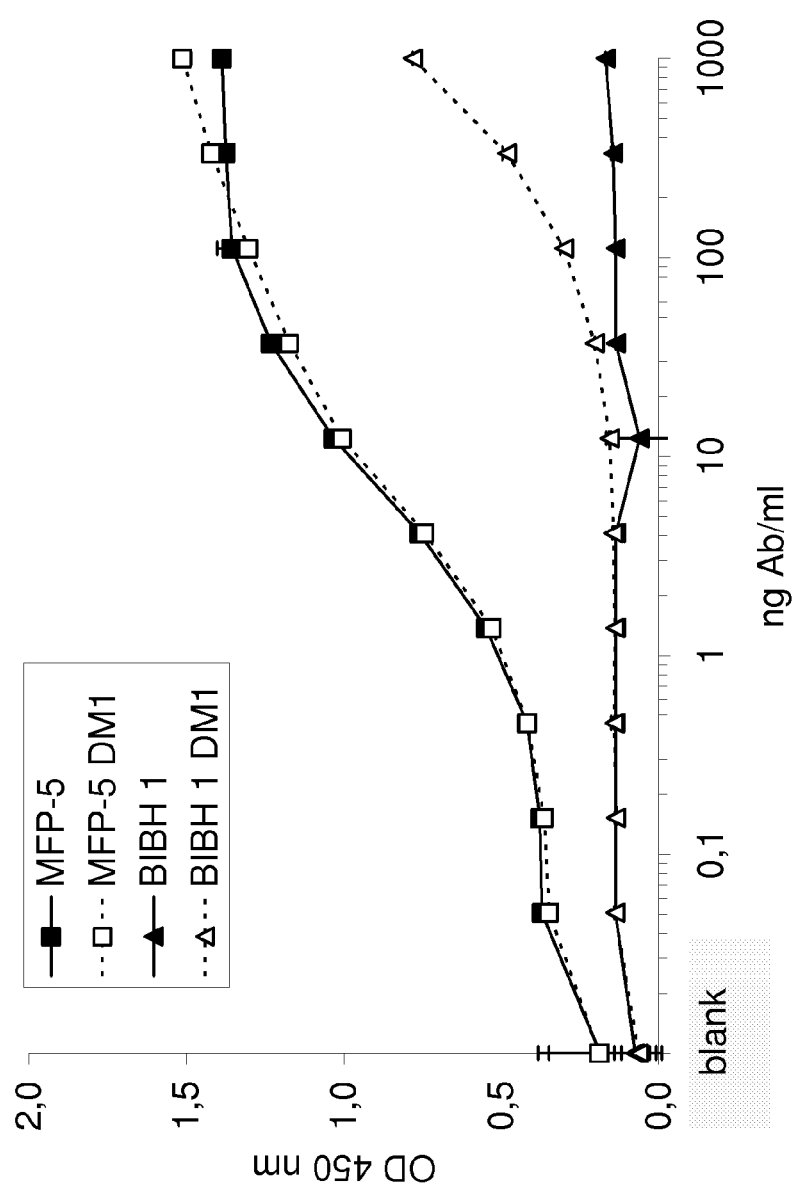
Figure 1C:
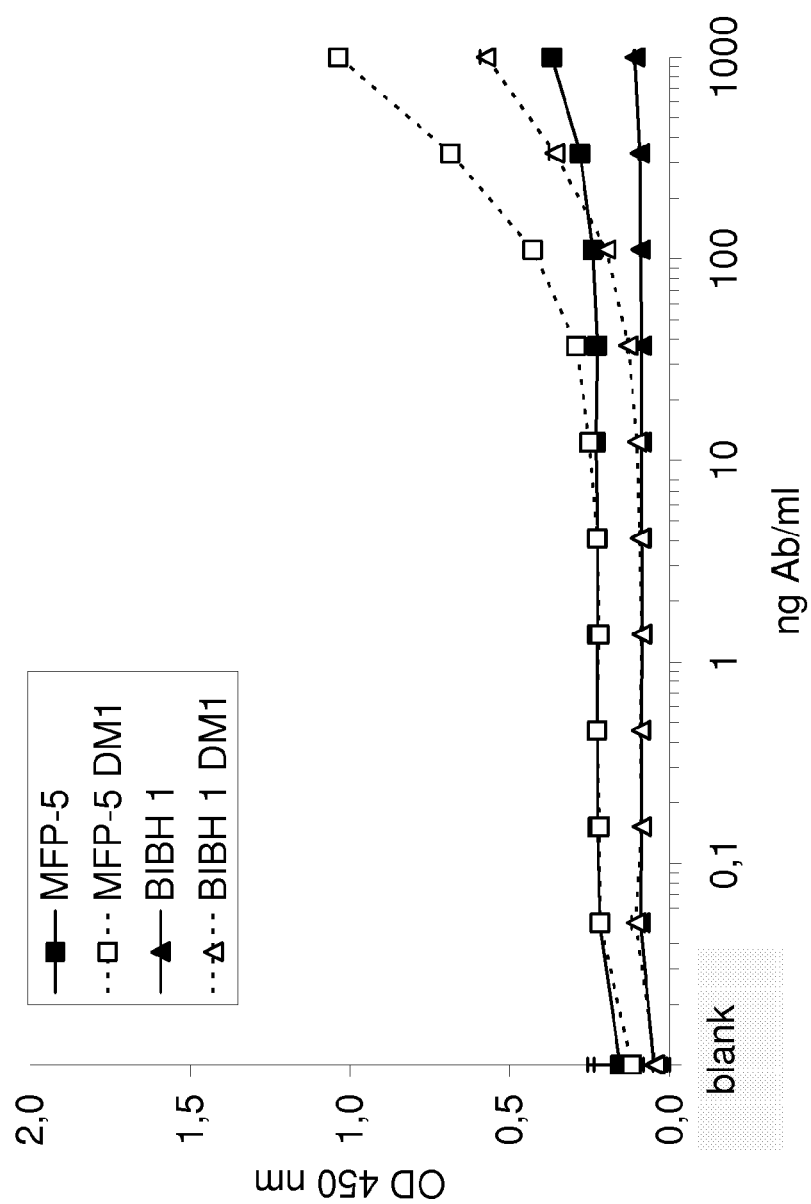

Analysis of In Vitro Binding of BIBH1-DM1 and MFP5-DM1 Compared to the Binding of the Parental Antibodies The binding of BIBH1 and MFP5 antibodies and the respective antibody conjugates BIBH1-DM1 and MFP5-DM1 to antigen positive and negative HT1080 cells is determined in a cell-ELISA assay. Binding to human FAP is monitored on the recombinant HT1080 v1.33 cell line and binding to murine FAP on the recombinant cell line HT1080 clone 13.6. For generation of HT1080 13.6, murine FAP cDNA is cloned (Niedermeyer et al. 1998) and ligated into the expression plasmid pZeoSV2(+) (Invitrogen). Stable clones are generated as described for HT1080 v1.33 and clones positive for murine FAP are screened with the murine FAP specific monoclonal antibody 3D11 (Niedermeyer et al., 2000). For the cell ELISA 100 µl of cell suspensions at various cell densities are seeded per well of a 96-well microliter plate and the cells are incubated overnight in an incubator (37° C., 5% CO2). On the next day, cells are fixed with 100% ethanol. Dilutions of the antibodies BIBH1 and MFP5 and of the conjugates BIBH1-DM1 and MFP5-DM1 are added in duplicates and incubated for two hours. After washing three times with PBS/Tween, diluted rabbit anti-human-IgG-peroxidase conjugate is added for detection of the BIBH1 antibodies and for detection of the MFP5 antibodies a diluted goat anti-mouse-Ig-peroxidase conjugate is added. After incubation for two hours at RT plates are washed again three times with PBS/Tween and bound anti-FAP-antibodies detected by addition of TMB staining solution. As shown in FIG. 1, the conjugation with DM1 does not alter the binding affinity of the antibodies BIBH1 and MFP5. Furthermore, FIG. 1 shows that MFP5, but not BIBH1, binds to both human and murine FAP:

A: Binding to HT1080 v1.33 expressing human FAP. The binding affinity of the antibodies is retained after conjugation to DM1.

B: Binding to HT1080 13.6 expressing murine FAP. Only the murine specific antibody MFP5 binds.

C: Negative control. The parental cell line HT1080 shows no endogenous FAP expression.

EXAMPLE 3

In Vitro Cytotoxicity Assay

100 µl of cell suspensions of HT1080 and the FAP positive clone HT1080 v1.33 at various cell densities are seeded per well of a 96-well microtiter plate and the cells are incubated overnight in an incubator (37° C., 5% CO2). On the next day dilutions of the cytotoxic conjugate MFP5-DM1 are added in duplicates and the cells are incubated for further three days. Remaining cells are stained by MTS and the signal read in a microliter plate spectrophotometer. The concentration resulting in 50% cytotoxic effect (EC50) is calculated using the graphing software GraphPad Prism (GraphPad Software, Inc., San Diego, Calif., USA) using a sigmoidal curve fit.

MFP5-DM1 is highly effective in killing the antigen-positive cell line HT1080 v1.33, with EC50 values of about 0.04 nM. The antigen-negative cell line HT1080 is effected by the conjugate only at much higher concentrations with an EC50 of about 59 nM.

EXAMPLE 4

In Vivo Anti-Tumour Efficacy of MFP5-DM1 Immunoconjugate Against Human Kidney Tumour Xenografts Expressing Human FAP In vivo anti-tumour efficacy of MFP5-DM1 is tested in a nude mouse model applying the recombinant human kidney tumour HEK293 FAP (human embryonic kidney cells, ATCC, Cat. No. CRL-1573, transfected with human FAP cDNA as described by Park et al., 1999). The cells are cultured in RPMI 1640 medium containing 10% fetal calf serum and supplements. $1 \times 10^7$ tumour cells (100 µl) are added to 100 µl matrigel and transplanted subcutaneously into the right flank of 6 week old female NMRI-nu/nu mice. Treatment starts when the tumours reach an average size of 291 mm³. Treatment consists of i.v. injections of MFP5-DM1 at a dose level of 300 µg DM1/kg given daily on five consecutive days (one cycle). PBS-treated animals serve as tumour growth control. Tumour growth is monitored by measuring tumour size. A tumour response is rated as complete response when the tumour completely disappeared at any time after start of treatment.

The average tumour volume of both groups during the observation period is measured. In the group treated with MFP5-DM1, the T/C (median tumor volume of treated animals divided by the median tumor volume of control animals) on day 42 is markedly decreased; a number of animals shows complete tumour regression. The obtained results show that the MFP5-DM1 displays excellent anti-tumour activity against human tumours expressing FAP.

EXAMPLE 5

In Vivo Anti-Tumour Efficacy of MFP5-DM1 Immunoconjugate Against Human Sarcoma Tumour Xenografts Expressing FAP
A. In Vivo Anti-Tumour Efficacy of MFP5-DM1 Immunoconjugate Against HT1080 Human Fibrosarcoma Tumours Expressing Human FAP In vivo anti-tumour efficacy of MFP5-DM1 is tested in a nude mouse xenograft model applying the FAP-expressing human tumour cell line HT1080 v1.33 (human fibrosarcoma). The cells are cultured in RPMI 1640 medium containing 10% fetal calf serum and supplements. $5 \times 10^6$ tumour cells are transplanted subcutaneously into the right flank of 6 week old female NMRI-nu/nu mice. Treatment starts when the tumours reach an average size of 29 to 38 mm$^3$. Treatment consists of i.v. injections of MFP5-DM1 given daily on 5 consecutive days. 2 different doses of MFP5-DM1 are tested in parallel in groups of 6 mice: 30 µg DM1/kg and 300 µg DM1/kg. PBS-treated animals serve as tumour growth control. Tumour growth is monitored by measuring tumour size.

A tumour response is rated as complete response when the tumour completely disappeared at any time after start of treatment.

The obtained results show that MFP5-DM1 induces excellent anti-tumour responses in HT1080 v1.33 xenografted nude mice.
B. In Vivo Anti-Tumour Efficacy of MFP5-DM1 Immunoconjugate Against Human Malignant Fibrous Histiocytoma Expressing Human FAP In vivo anti-tumour efficacy of MFP5-DM1 is tested in a nude mouse xenograft model applying the antigen-positive human tumour MFSH (MFSH cell line: human malignant fibrous histiocytoma (Takeya et al. 1995; Iwasaki et al. 1992).

The cells are cultured in RPMI 1640 medium containing 10% fetal calf serum and supplements. $1 \times 10^7$ tumour cells are transplanted subcutaneously with matrigel into the right flank of 6 week old female NMRI-nu/nu mice. For therapy experiments tumours are maintained via passaging of tumour fragments. Treatment started when the tumours reached an average size of 116-131 mm$^3$. Treatment consists of i.v. injections of MFP5-DM1 given weekly for four weeks. 3 different dose levels of MFP5-DM1 are tested in parallel: 100 µg DM1/kg, 200 µg DM1/kg, and 400 µg DM1/kg. PBS treated animals serve as tumour growth control. One group is treated with unconjugated antibody MFP5 at a dose level corresponding to the antibody amount at the highest dose level of MFP5-DM1 immunoconjugate. Tumour growth is monitored by measuring tumour size.

These results show that MFP5-DM1 conjugate induces anti-tumour responses in MSFH xenografted nude mice when given once a week over a period of four weeks, with dose-dependent response. Unconjugated antibody shows no anti-tumour effect in this experiment.
C. In Vivo Anti-Tumour Efficacy of MFP5-DM1 Immunoconjugate Against a Human Osteosarcoma Tumour Xenograft Expressing Human FAP In vivo anti-tumour efficacy of MFP5-DM1 is tested in a nude mouse xenograft model applying a tumour derived from a human osteosarcoma. For therapy experiments tumours are maintained via passaging of tumour fragments.

Passaged tumours are transplanted subcutaneously into the right flank of 6 week old female NMRI-nu/nu mice. Treatment starts when the tumours reach an average size of 75-95 mm$^3$. Mice are randomised into three different treatment groups (three different dose levels, 8 mice per group):

Treatment consists of i.v. injections of MFP5-DM1 given daily on five consecutive days, starting at day 1. Three different dose levels of MFP5-DM1 are tested: 30 µg DM1/kg, 100 µg DM1/kg and 200 µg DM1/kg. Control animals are either untreated (PBS) or treated with unconjugated antibody MFP5 at a dose level corresponding to the antibody amount at the highest dose level of MFP5-DM 1 immunoconjugate. Tumour growth is monitored by measuring tumour size.

The obtained results show that MFP5-DM1 induces anti-tumour responses in osteosarcoma-xenografted nude mice when given daily on five consecutive days, with dose-dependent response. Unconjugated antibody shows no antitumour effect in this experiment.

EXAMPLE 6

In Vivo Anti-Tumour Efficacy of MFP5-DM1 Immunoconjugate Against Human Tumour Xenografts not Expressing Human FAP In vivo anti-tumour efficacy of MFP5-DM1 is tested in nude mice inoculated with human tumour cells not expressing FAP, derived from human pancreatic cancer (Example 5A), human non-small-cell lung cancer (Example 5B) and human head and neck cancer (Example 5C). Expression of FAP on stromal fibroblasts of mouse origin is verified by standard immunohistochemistry using chimeric MFP5.

For therapy experiments tumours are maintained via passaging of tumour fragments for the human pancreatic and lung cancer.
A: Human Pancreatic Cancer Xenograft Model in Nude Mice:

Passaged tumours are transplanted subcutaneously into the right flank of 6 week old female NMRI-nu/nu mice. Treatment started when the tumours reached a median size of 85-108 mm$^3$.

Mice are randomised into the following treatment groups (8 mice per group):
Group 1: Control (PBS)
Group 2: MFP5-DM1 (400 µg DM1/kg/d)
Group 3: MFP5-DM1 (200 µg DM1/kg/d)
Group 4: MFP5-DM1 (100 µg DM1/kg/d)
Group 5: MFP5 control (28 mg/kg/d)

Figure 2:
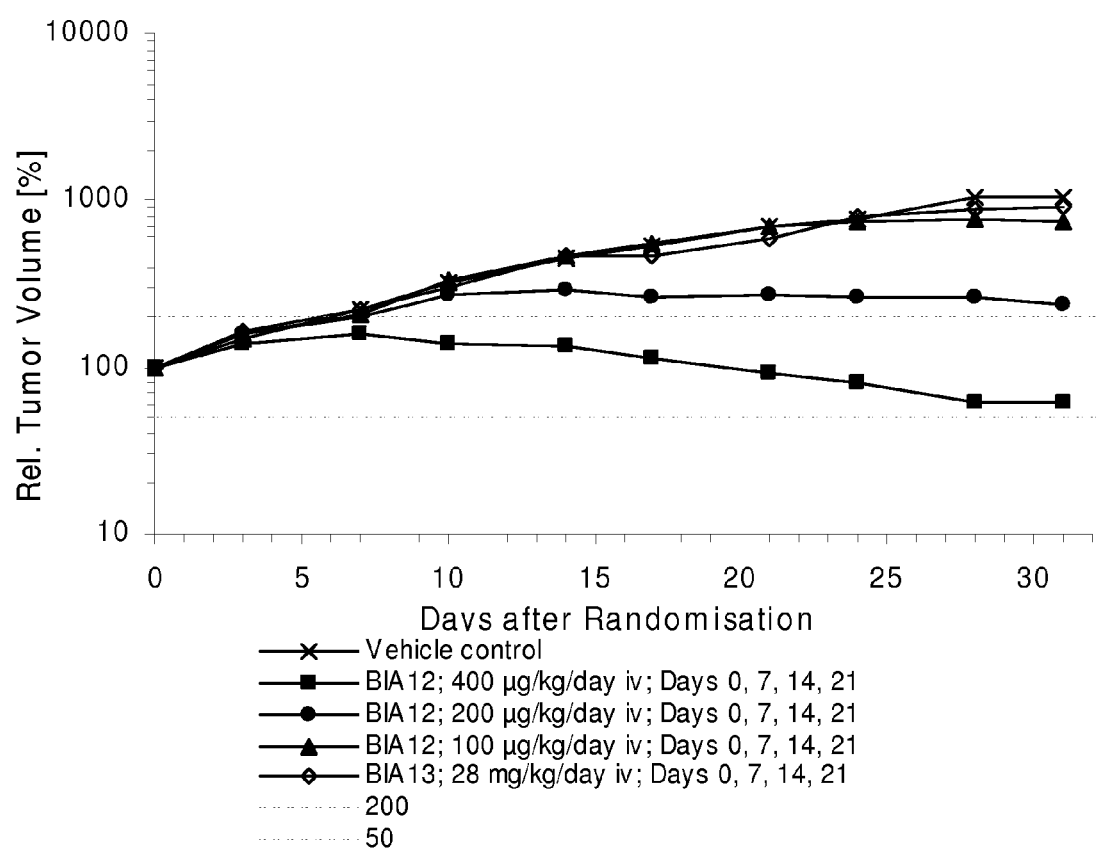
FIG. 2: Efficacy of MFP5-DM1 treatment in nude mice xenografted with human pancreatic tumours.

Treatment consists of i.v. injections of MFP5-DM1 given once a week (four consecutive weeks), starting at day 0.3 different dose levels of MFP5-DM1 are tested: 7 mg/kg MFP5 corresponding to 100 µg DM1/kg, 14 mg/kg MFP5 corresponding to 200 µg DM1/kg and 28 mg/kg MFP5 corresponding to 400 µg DM1/kg. Control animals are either untreated (PBS) or treated with unconjugated antibody (MFP5 control antibody, 28 mg/kg). Tumour growth is monitored by measuring tumour size. The relative tumour volume of each group during the observation period is shown in FIG. 2 (the relative tumour volumes per group are shown, the treatment groups are indicated; in this figure, BIA 12 designates the MFP5 conjugate, and BIA 13 designates the unconjugated antibody MFP5).

Tumours treated either with control antibody or at the low dose level of 7 mg/kg MFP5-DM1 show similar growth as untreated tumours with T/C (treatment vs. control) on day 31 of 86% for the control antibody and 71% for the low dose. In the groups treated with 14 mg/kg/d MFP5-DM1 and 28 mg/kg/d MFP5-DM1, dose-dependent efficacy is observed with T/C on day 31 of 22% for the group 3 treated with 14 mg/kg/d MFP5-DM1 and T/C of 6% on day 31 for the high dose group 4 treated with 28 mg/kg/d MFP5-DM1.

These results show that MFP5-DM1 induces excellent anti-tumour responses in mice xenografted with a human pancreatic carcinoma when given once a week over a period of four weeks, with dose-dependent response. Unconjugated antibody shows no antitumour effect in this experiment.

B: Human Non-Small-Cell Lung Cancer Xenograft Model in Nude Mice

Passaged tumours are transplanted subcutaneously into the right flank of 6 week old female NMRI-nu/nu mice. Treatment started when the tumours reached a median size of 92-120 mm$^3$.

Mice are randomised into the following treatment groups (8 mice per group):
Group 1: Control (PBS)
Group 2: MFP5-DM1 (400 µg DM1/kg)
Group 3: MFP5-DM1 (200 µg DM1/kg)
Group 4: MFP5-DM1 (100 µg DM1/kg)
Group 5: MFP5 (28 mg/kg)

Figure 3:
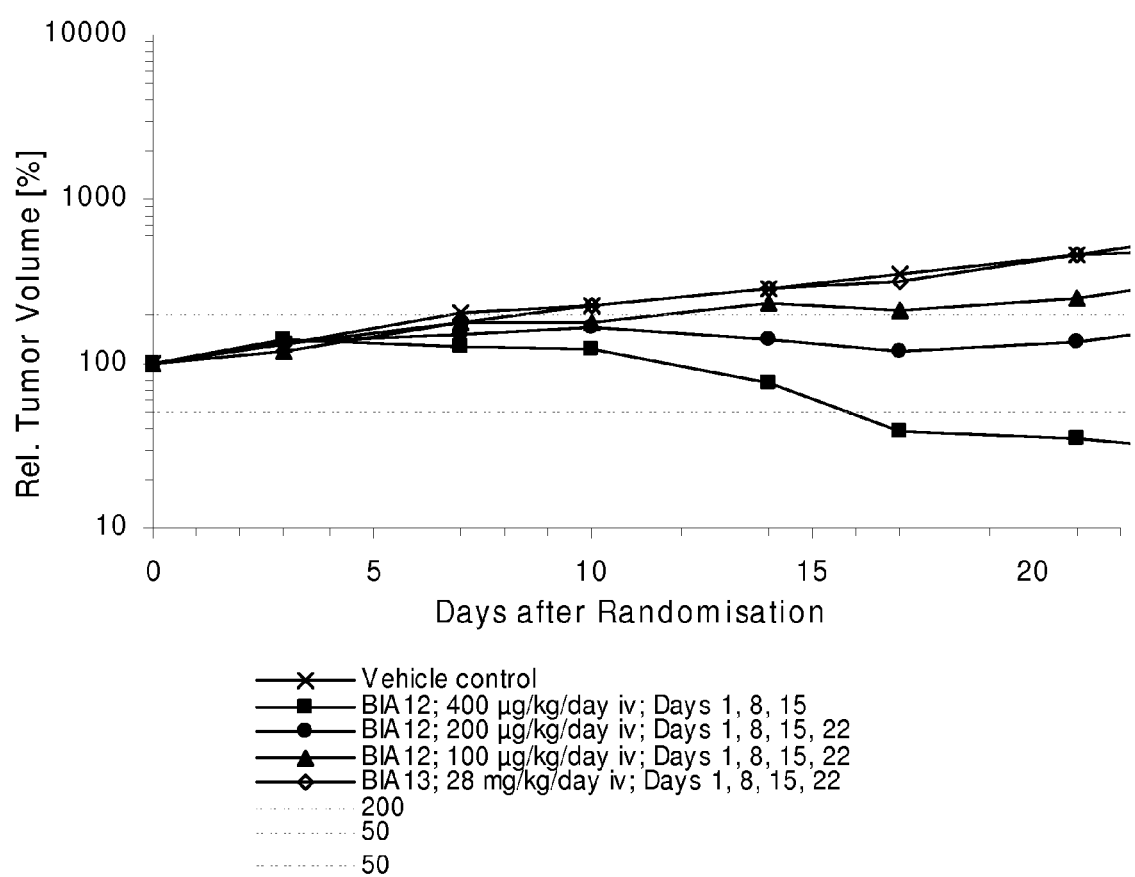
FIG. 3: Efficacy of MFP5-DM1 treatment in nude mice xenografted with human lung tumours.

Treatment consists of i.v. injections of MFP5-DM1 given once a week (four consecutive weeks), starting at day 0. Three different dose levels of MFP5-DM1 are tested in parallel: 7 mg/kg/d MFP5 DM1 conjugate corresponding to 100 µg DM1/kg, 14 mg/kg MFP5 DM1 conjugate corresponding to 200 µg DM1/kg and 28 mg/kg MFP5-DM1 conjugate corresponding to 400 µg DM1/kg. Control animals are either untreated (PBS) or treated with unconjugated antibody (MFP5 control antibody, 28 mg/kg). Tumour growth is monitored by measuring tumour size. The relative tumour volume of each group during the observation period is shown in FIG. 3 (the relative tumour volumes per group are shown, the treatment groups are indicated. In this figure, BIA 12 designates the MFP5 conjugate, and BIA 13 designates the unconjugated antibody MFP5). Tumours treated with control antibody showed similar growth as untreated tumours with T/C rates on day 21 of 107%. In the groups treated with 7, 14 or 28 mg/kg/d MFP5-DM1, dose-dependent efficacy is observed with T/C rates on day 21 of 7.6% for group 2 treated with 28 mg/kg/d MFP5-DM1, 29% for group 3 treated with 14 mg/kg/d MFP5-DM1 and 54% for group 4 treated with 7 mg/kg/d MFP5-DM1.

These results show that MFP5-DM1 induces excellent anti-tumour responses against human lung tumours in xenografted nude mice when given once a week over a period of four weeks, with dose-dependent response. Unconjugated antibody shows no antitumour effect in this experiment. Tumour sections from treated animals stained with hematoxylin show drastic reduction of tumour cells.

C: Human Head and Neck Cancer Xenograft Model in Nude Mice:

In vivo anti-tumour efficacy of MFP5-DM1 is tested in a nude mouse xenograft model applying the human tumour cell line FaDu (human head and neck cancer). The cells are cultured in RPMI 1640 medium containing 10% fetal calf serum and supplements. 1×10$^6$ tumours cells are transplanted subcutaneously into the right flank of 6-8 week old female NMRI-nu/nu mice. Treatment started when the tumours reached a median size of 72-78 mm$^3$.

Mice are randomised into the following treatment groups (6 mice per group):
Group 1: Control (PBS)
Group 2: MFP5-DM1 (200 µg DM1/kg/d)
Group 3: MFP5-DM1 (400 µg DM1/kg/d)
Group 4: MFP5 control (17 mg/kg/d)

Figure 4:
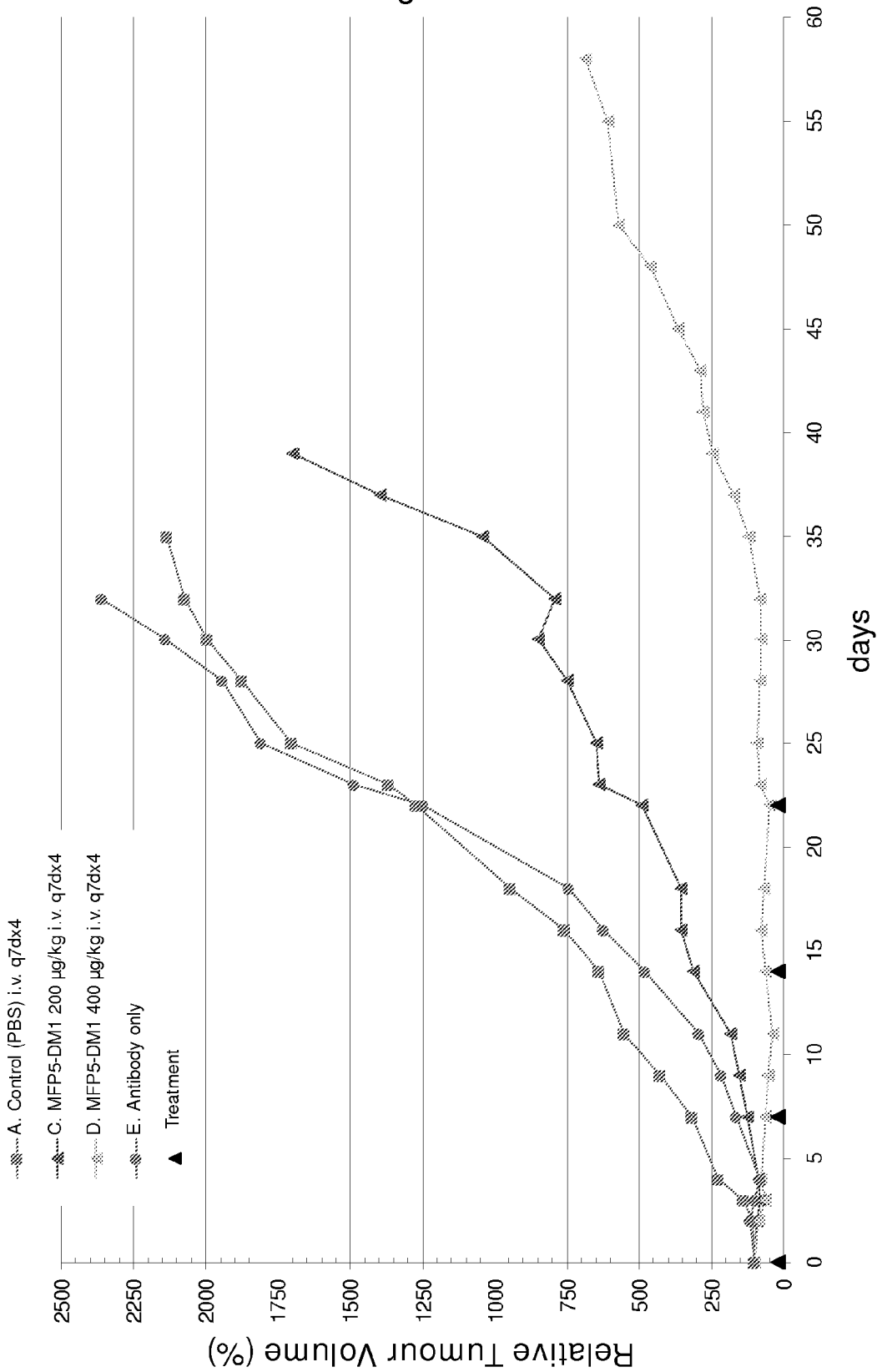
FIG. 4: Efficacy of MFP5-DM1 treatment in nude mice xenografted with human head and neck tumours.

Treatment consists of i.v. injections of MFP5-DM1 given once a week (four consecutive weeks), starting at day 0.2 different dose levels of MFP5-DM1 are tested: 8.5 mg/kg MFP5 corresponding to 200 µg DM1/kg and 17 mg/kg MFP5 corresponding to 400 µg DM1/kg. Control animals are either untreated (PBS) or treated with unconjugated antibody (MFP5 control antibody, 17 mg/kg). Tumour growth is monitored by measuring tumour size. The relative tumour volume of each group during the observation period is shown in FIG. 4 (the relative tumour volumes per group are shown, the treatment groups are indicated).

Tumours treated with control antibody show similar growth as untreated tumours. In the groups treated with 8.5 mg/kg/d MFP5-DM1 and 17 mg/kg/d MFP5-DM1, dose-dependent efficacy is observed with T/C on day 32 of 40% for the group 2 treated with 8.5 mg/kg/d MFP5-DM1 and T/C of 10% on day 32 for the high dose group 3 treated with 17 mg/kg/d MFP5-DM1.

These results show that MFP5-DM1 induces excellent anti-tumour responses in mice xenografted with a human head and neck cancer when given once a week over a period of four weeks, with dose-dependent response. Unconjugated antibody shows no antitumour effect in this experiment.

EXAMPLE 7

Comparison of MFP5-Maytansinoid Immunoconjugates Containing Three Different Linkers in Their In Vivo Anti-Tumour Efficacy Against Human Tumour Xenografts not Expressing Human FAP To elucidate the mechanism of action of an MFP5 maytansinoid conjugate, additional conjugates of MFP5 are generated using the same maytansinoid, DM1, but instead of being coupled by SPP (disulfide linkage), the toxin is coupled to the antibody via the "non-cleavable" thioester linker SMCC, as well as a modified maytansinoid, DM4, coupled via the cleavable disulfide-containing SPDB linker. (Recent studies have shown that an SPDB-DM4 conjugate, but not an SMCC-DM1 conjugate of the same antibody, generate metabolites that potently kill bystander cells.)

For the experiments in this Example, MFP5-SPDB-DM4 and MFP5-SMCC-DM1 are generated and characterized in vitro and in vivo, as described above for MFP5-DM1, the conjugate containing a disulfide bond. Whereas the SPDB linker used in MFP5-DM4, similar to the SPP linker used in MFP5-DM1, contains a cleavable disulfide bond, a non-cleavable thioether bond is present in the SMCC linker. In proliferation assays, both MFP5-DM4 and MFP5-SMCC-DM1 show similarly high potency and selectivity as MFP5-DM1 (EC50=29 pM and 22 pM, respectively, on FAP-expressing HT1080 cells; >1 µM on FAPα-negative parental cells).

Figure 5:
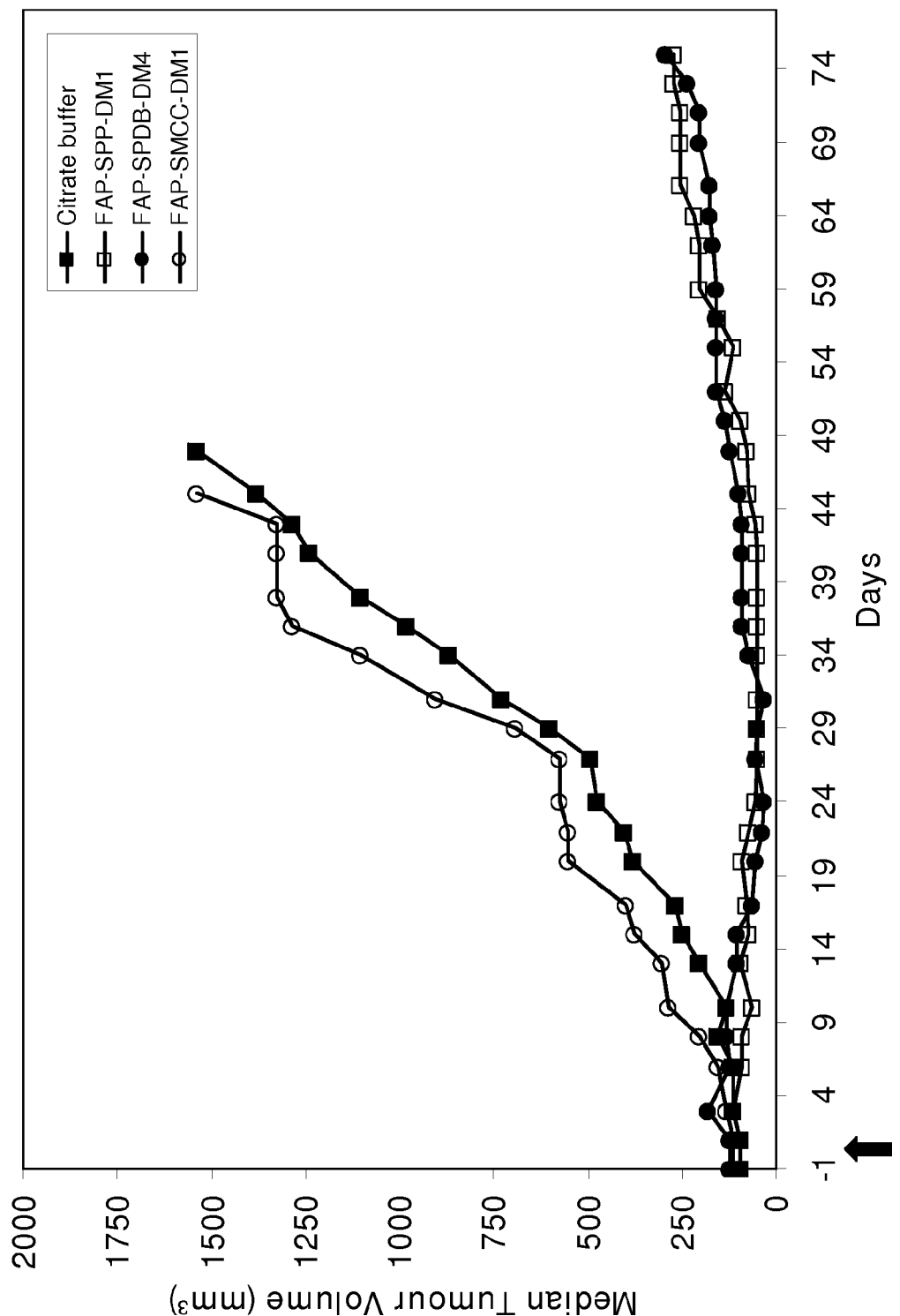
FIG. 5A: Comparison of efficacy MFP5 maytansinoid conjugates with 3 different linkers in treatment of nude mice xenografted with human pancreatic cancer.
FIG. 5B: Comparison of efficacy MFP5 maytansinoid conjugates with 3 different linkers in treatment of nude mice xenografted with human lung cancer.
FIG. 5C: Comparison of efficacy MFP5 maytansinoid conjugates with three different linkers in treatment of nude mice xenografted with human head and neck tumours.
Figure 5:
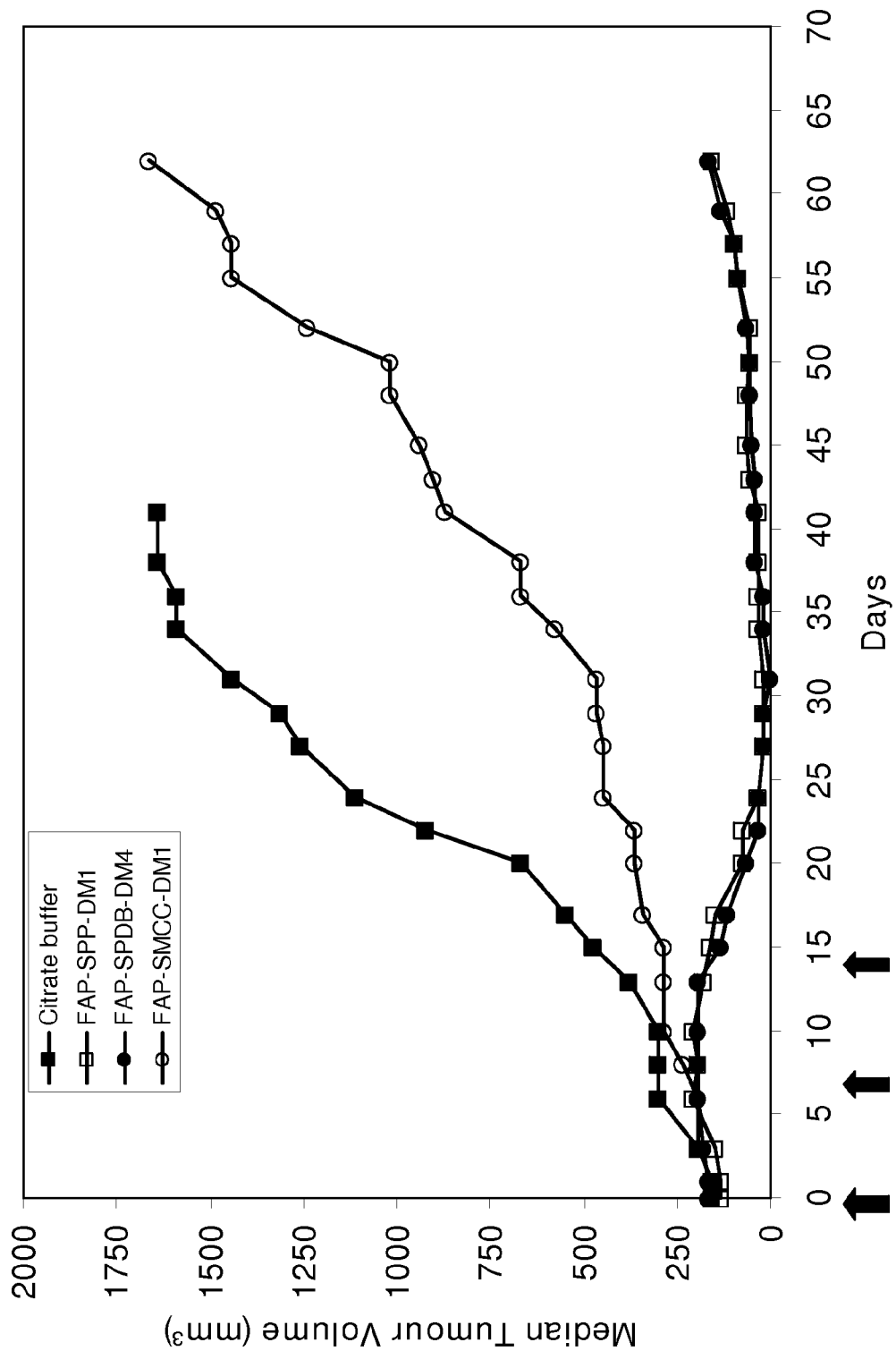
Figure 5:
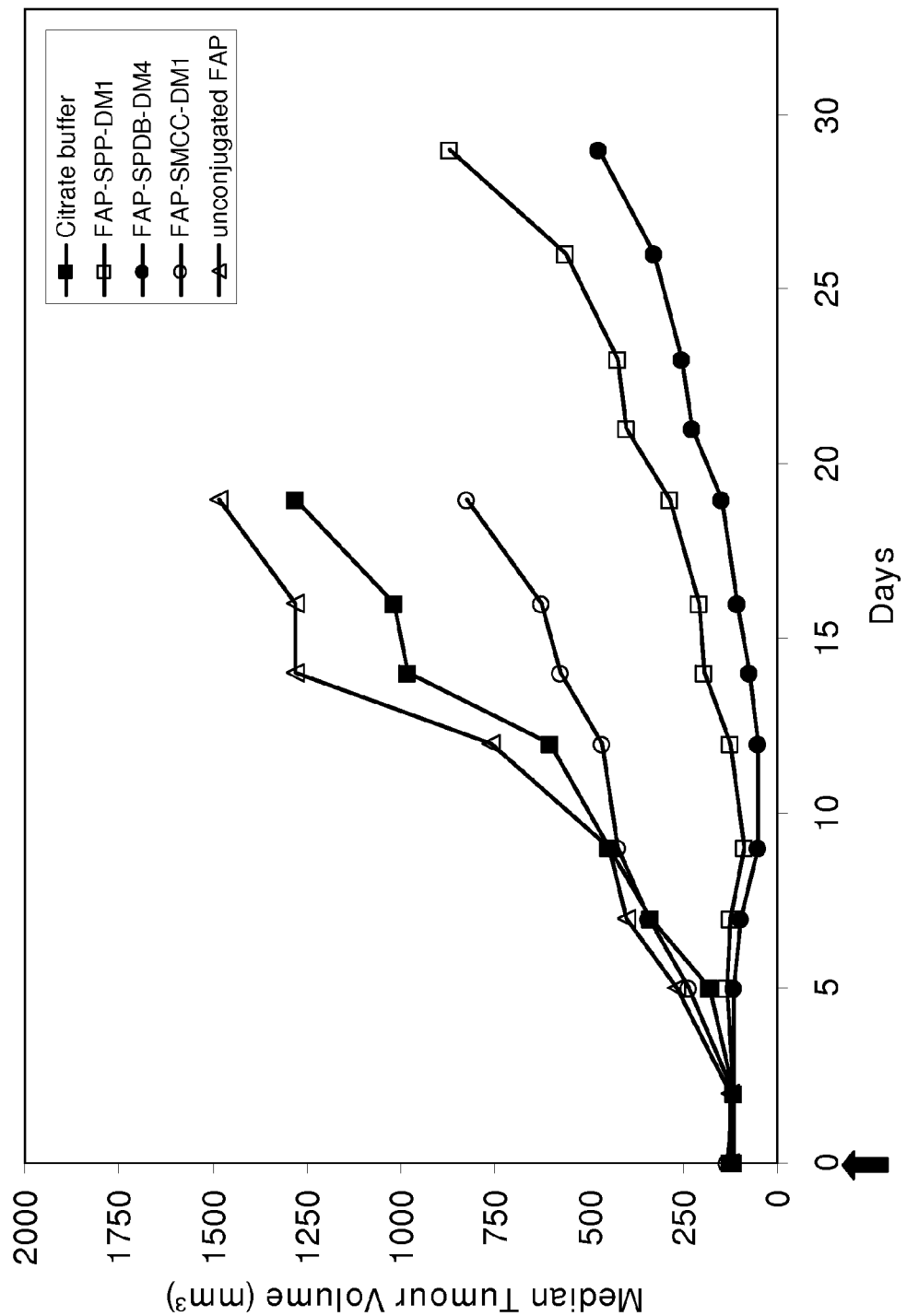

In the pancreas adenocarcinoma model, a single dose of MFP5-DM1 or MFP5-DM4, equivalent to 800 µg maytansinoid/kg, respectively, results in regression of tumors, including complete regression in 3 out of 8 treated animals (FIG. 5A). FIG. 5A shows the growth kinetics of the xenografted human pancreatic tumors during treatment. Mice are treated i.v. with citrate buffer (closed square); mAbFAP5-DM1 (open square), mAbFAP5-DM4 (closed circle), mAbFAP5-SMCC-DM1 (closed circle). Tumor sizes are represented as the median of eight mice. Arrows indicate the treatment. As can be seen FIG. 5A, the remaining tumors eventually resume growth, but at a slow rate that was maintained until the end of the experiment on day 75 post-treatment. In contrast, the uncleavable MFP5-SMCC-DM1 conjugate at the same dose level does not show any significant efficacy.

In the lung carcinoma model (FIG. 5B), the conjugates are dosed at 400 µg maytansinoid per kg administered once weekly for three weeks. FIG. 5B shows the growth kinetics of xenografted human lung tumors during treatment. Mice were treated i.v. with citrate buffer (closed square); mAbFAP5-DM1 (open square), mAbFAP5-DM4 (closed circle), mAb-FAP5-SMCC-DM1 (closed circle). Tumor sizes are represented as the median of eight mice. Arrows indicate the treatment. Again, it can be observed that MFP5-DM1 as well as the MFP5-DM4 conjugate induce tumor regressions, including complete regressions in 4/8 and 4/8 treated animals, respectively, and the growth rate of residual tumors is reduced until the end of the experiment on day 62. Regrowth of 2 tumors is observed in both groups.

An additional xenograft experiment is performed, using the head and neck carcinoma cell line FaDu. Subcutaneous FaDu xenografts in nude mice induce a less prominent stromal reaction in the host in comparison to the other tumor models, however FAPα expression is consistently upregulated in the tumor stromal fibroblasts. Following a single administration of conjugates at a dose of 600 µg maytansinoid/kg, MFP5-DM1 and the MFP5-DM4 conjugate, but not the MFP5-SMCC-DM1 conjugate, show significant efficacy, and complete tumor regressions are observed in 1/8 and 2/8 of the treated animals, respectively. FIG. 5C shows the growth kinetics of xenografted human head and neck tumors during treatment. Mice are treated i.v. with citrate buffer (closed square); mAbFAP5-DM1 (open square), mAbFAP5-DM4 (closed circle), mAbFAP5-SMCC-DM1 (closed circle) and unconjugated antibody (open diamond). Tumor sizes are represented as the median of eight mice. Arrows indicate the treatment. In all experiments, treatment is well tolerated and weight gain of the animals is similar to that in the control group. The reason for this finding may be due to the fact that the cleavable linkers have a higher bystander effect potential (whereas the uncleavable linker normally is less toxic and therefore offers a larger therapeutic window).

The experiments in the three tumor xenograft models described in this Example demonstrate, at the given dose and the conditions of this experiment, that MFP5 conjugates containing SPP-DM1 or SPDB-DM4 are highly efficacious in delaying tumor growth or inducing tumor regression, whereas the SMCC-DM1 conjugate is essentially devoid of efficacy. These results thus further substantiate the bystander killing hypothesis; however, it is possible that bystander effects (malignant cells, endothelial cells) and direct effects on stromal fibroblasts synergise to achieve the anti tumor responses observed in this experiment.

EXAMPLE 8

Humanisation of MFP5

To establish a structural model of the MFP5 VL domain, a structural template is chosen from the Protein Data Bank (PDB) of Brookhaven National Laboratory. The VL domain from the murine monoclonal antibody entry "1FOR" is chosen with 83% sequence identity/88% similarity and 2.8 Å resolution. For the MFP5 VH domain, the mouse monoclonal antibody structure "2C1P" with 71% sequence identity and 81% similarity is chosen as the main modeling template. To determine the structure of the H-CDR3 as separate model, the murine monoclonal antibody structure "1MAM" is chosen for the loop graft. The best fit for human consensus framework is of the type human Vk and human VH3, 15 such structures are available in the PDB. For establishing a structure model of the human Vk3 domain, the human antibody structure "1DNO" is chosen. For modeling a human VH1 domain, the PDB entry "1VGE" is chosen and in addition the structure of "1WT5" is used to model the N-terminus and the PDB entry "1FVC" for the CDR H3 loop. Loop grafting is performed by embedding the murine MFP5 CDR regions into human antibody frameworks and the following humanized chains constructs are synthesized:

SEQ ID NO:6: heavy chain (hVH01); SEQ ID NO:7: light chain, version 1 (hVK03-version1); SEQ ID NO:8: light chain, version 2 (hVK03-version2).

The humanized variable regions are cloned into immunoglobulin expression vectors (pcDNA3.1 Invitrogen, containing human IgG1 heavy and human kappa light chain constant regions respectively) and transiently co-transfected in the combinations of hVH01+hVK03-version1 and hVH01+hVK03-version2, both combinations are transiently expressed in the HEK 293 freestyle expression system (Invitrogen) and purified on protein A columns.

Affinity of the obtained humanized anti-FAP antibodies to FAP is determined by surface plasmon resonance (Biacore), resulting in KD values of 30-40 nM. Approximately 200 resonance units anti-mouse IgG antibody are immobilized using the amine coupling kit on a CM5-biosensor-chip in a Biacore 2000 (all materials Biacore AB, Uppsala, Sweden). MFP5 is bound to the sensor chip by application of a solution with 5.2 µg/ml for 3 minutes. Association and dissociation of recombinant human, FAP is measured for 5 minutes at concentrations from 3.7-300 nM. Running buffer is HBS-EP (Biacore) supplemented with 1.25% CM-Dextran (Fluka) and 0.025% bovine serum albumine (Serva) at a flow of 20 µl/min. Surface regeneration is performed using 50 mM HCl for 30 sec.

Affinity parameters are calculated using the separate cure fit algorithm of the BIAevaluation software, version 4.1 (Biacore).

EXAMPLE 9

Expression of FAP in Thyroid Cancers

Figure 6:
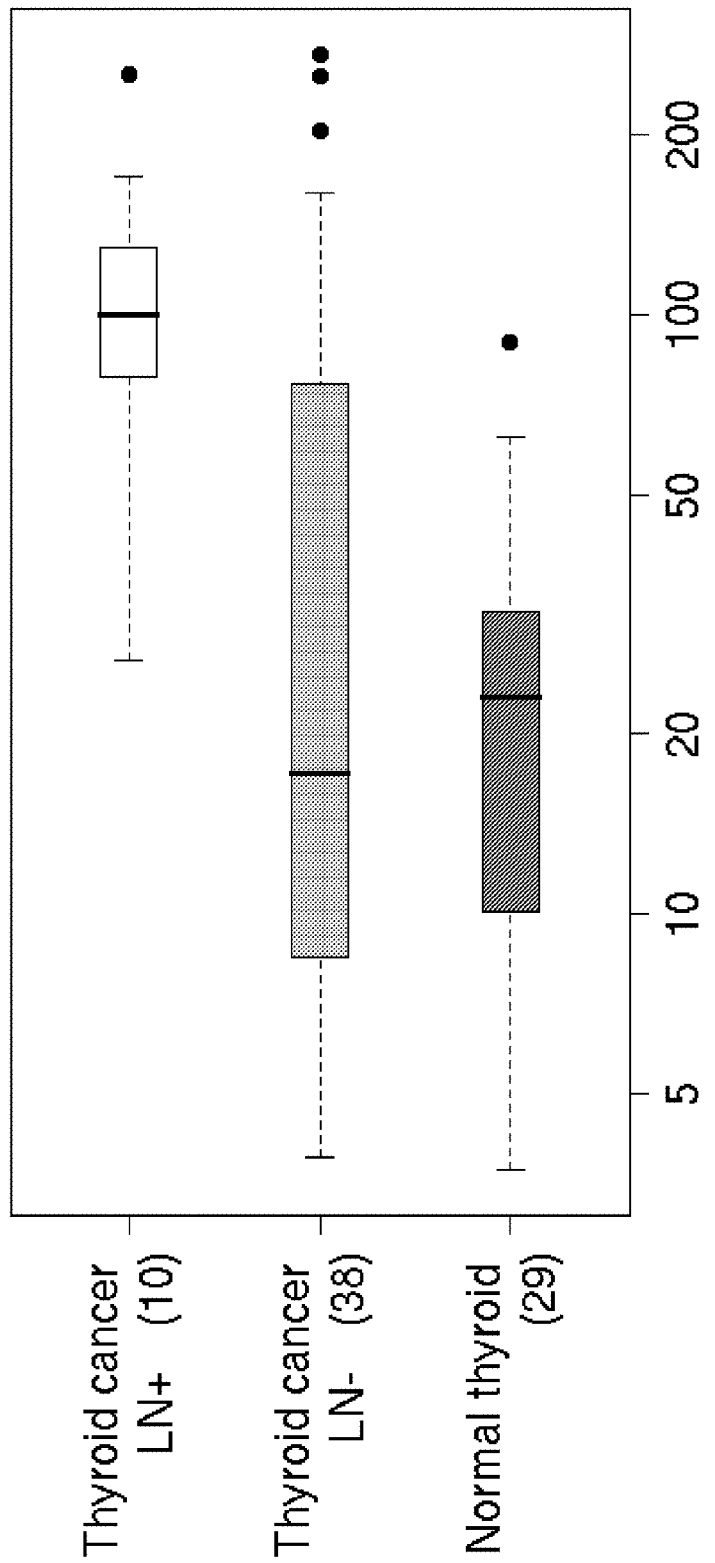
FIG. 6: Expression of FAP in thyroid cancers

The mRNA expression levels of FAPα in 38 thyroid cancer samples from patients without lymph node metastasis (LN−; including 3 anaplastic carcinomas, 6 follicular carcinomas, 2 medullary carcinomas and 37 papillary carcinomas) and 10 thyroid cancer samples from patients with lymph node metastasis (LN+; including 9 papillary carcinomas and one anaplastic cancer) are determined by means of oligonucleotide chip technology, and visualized. (As a control set, 29 normal thyroid tissue samples were used). FIG. 6 shows that FAPα is overexpressed in cancer samples, it is significantly over-expressed in tumors from patients with lymph node metastasis.

Box- and whisker plots are generated with the statistical computing package R based on normalized gene expression data extracted from the BioExpress™ database (Gene Logic Inc., Gaithersburg, Md., USA). The bold center line in the box indicates the median, its left and right boundaries showing the first and third quartile of the data. Whiskers extend to the most extreme data point which is no more than 1.5 times the interquartile range. The human sample collection has been described by the originator of the BioExpress™ database. The respective hybridizations are performed on Affymetrix HG-U133A/B oligonucleotide chips (Affymetrix Inc., Santa Clara, Calif., USA).

References

Boulianne G. L., Hozumi N. and Shulman, M. J., (1984). Production of functional chimeric mouse/human antibody. *Nature* 312: 643.

Carlsson et al., *Biochem. J.* 173: 723-737 (1978).

Catty D. Antibodies. *Oxford IR Press* 1988.

Chari R V J, Martell B A, Gross J L, Cook S B, Shah S A, Blättler WA, McKenzie S J, Goldmacher V S. Immunoconjugates containing novel maytansinoids: promising anticancer drugs. *Cancer Research* 52: 127-31, 1992.

Chari R V J, Derr S M, Steeves R M, Widdison W C: Dose-response of the anti-tumour effect of HUN901-DM1 against human small cell lung cancer xenografts. *Proceedings of the American Association of Cancer Research* (2000) 41, (April 1-5), Abs. 4405.

Chothia and Lesk., *J. Mol. Biol.* 196: 901-917 (1987).

Emini, E A, Hughes, J, Perlow, D, and Boger, J, (1985). *J. Virol.* 55, 836-839.

Francisco et al., *Blood.* 2003 Aug. 15; 102(4):1458-65.

Frank, et al., *Methods Enzymol.* 154: 221-249 (1987).

Gait, M. J., Oligonucleotide Synthesis. A Practical Approach. IRL Press, Oxford, UK (1984).

Garin-Chesa P., Old L. J., and Rettig W. J., (1990), Cell surface glycoprotein of reactive stromal fibroblasts as a potential antibody target in human epithelial cancers. *Proc. Natl. Acad. Sci.* 87: 7235.

Goldmacher et al., *J Immunol* 135: 3648-3651, (1985).

Goldmacher et al., *J Cell Biol* 102: 1312-1319, (1986).

Hayden and Mandecki. Gene synthesis by serial cloning of oligonucleotides. *DNA* 7(8): 571-7 (1988).

Heider, K.-H., Hofmann, M., Horst, E., van den Berg, F., Ponta, H., Herrlich, P., and Pals, S. T. A human homologue of the rat metastasis-associated variant of CD44 is expressed in colorectal carcinomas and adenomatous polyps. *J. Cell Biol.* 120: 227-233 (1993).

Hotheinz R, Al-Batran S E, Hartmann F, Hartung G, Jager D, Renner C, Tanswell P, Kunz U, Amelsberg A, Kuthan H, Stehle G: Stromal antigen targeting by a humanised monoclonal antibody: An early phase II trial of sibrotuzumab in patients with metastatic colorectal cancer, *Onkologie* 26: 44-48, (2003).

Ichimura et al., *J. Antibiot.* (Tokyo), 44, 1045-53 (1991).

Iwasaki H et al. *Cancer* 1992, 15: 437-447.

Jameson, B A and Wolf, H. (1988), "The antigenic index: a novel algorithm for predicting antigenic determinants." *Comput. Appl. Biosci.* 4, 181-186.

Johnson S, Bird R E. Construction of single-chain derivatives of monoclonal antibodies and their production in *Escherichia coli. Methods Enzymol.* 203: 88-98 (1991).

Jones S T, Bendig M M: Rapid PCR-cloning of full length mouse immunoglobulin variable regions, *Biotechnology* 9, 88-89, 1991).

Kabat E. A., Wu T. T., Perry H. M., Gottesman K. S, and Foeller C. Sequences of Proteins of Immunological Interest (5th Ed.). NIH Publication No. 91-3242. U.S. Department of Health and Human Services, Public Health Service, National Institutes of Health, Bethesda, Md. (1991).

Koopman, G., Heider, K.-H., Horts, E., Adolf, G. R., van den Berg, F., Ponta, H., Herrlich, P., Pals, S. T. Activated human lymphocytes and aggressive Non-Hodgkin's lymphomas express a homologue of the rat metastasis-associated variant of CD44. *J. Exp. Med.* 177: 897-904 (1993).

Kreitman R J Hansen H J, Jones A L, FitzGerald D J P, Goldenberg D M, Pastan I. *Pseudomonas* exotoxin-based immunotoxins containing the antibody LL2 or LL2-Fab' induce regression of subcutaneous human B-cell lymphoma in mice. *Cancer Res.* 53: 819-825 (1993).

Kupchan et al., *J. Med. Chem.*, 21, 31-37 (1978).

Kyte, J. and Doolittle, R F., (1982), *J. Mol. Biol.* 157, 105-132.

Lambert J M, Derr S M, Cook S, Braman G, Widdison W, Chari R V J. Pharmacokinetics, in vivo stability, and toxicity of the Tumour-activated prodrug, C242-DM1, a novel colorectal cancer agent. *Proceedings of the American Association of Cancer Research* (1998) 39: Abs 3550.

Liu C, Tadayoni B M, Bourret L A, Mattocks K M, Derr S M, Widdison W C, Kedersha N L, Ariniello P D, Goldmacher V S, Lambert J M, Blättler W A, Chari R V J. Eradication of large colon tumour xenografts by targeted delivery of maytansinoids. *Proc Natl Acad Sci USA* 93: 8618-23, (1996).

Niedermeyer J, Enenkel B, Park J, Lenter M C, Rettig W J, Klaus Damm, Schnapp A: Mouse Fibroblast Activation Protein. Conserved Fap gene organization and biochemical function as a serine protease, *Eur. J. Biochem.* 254, 650-654, (1998).

Niedermeyer J, Kriz M, Hilberg F, Garin-Chesa P, Bamberger U, Lenter M C, Park J, Viertel B, Püschner H, Mauz M, Rettig W J, Schnapp A: Targeted Disruption of Mouse Fibroblast Activation Protein. Molecular and Cellular Biology 20: 1089-1094, (2000).

Park J, Lenter M C, Zimmermann R N, Garin-Chesa P, Old L J, Rettig W J: Fibroblast Activation Protein, a dual specificity serine protease expressed in reactive human tumour stromal fibroblasts. *JBC,* 274, 36505-36512, (1999).

Rettig W R, Garin-Chesa P, Beresford R, Oettgen H F, Melamed M R, Old L J: Cell-surface glycoproteins of human sarcomas: Differential expression in normal and malignant tissues and cultured cells, *PNAS* 85, 3110-3114, 1988).

Revets H, De Baetselier P, Muyldermans S. (2005 January). Nanobodies as novel agents for cancer therapy. *Expert Opin Biol Ther.* 5(1): 111-24.

Sasse et al., *J. Antibiot.* (Tokyo), 53, 879-85 (2000).

Scott A W, Wiseman G, Welt S, Lee F-T, Hopkins W, Mitchell P, Adjei A, Divgi C, Larson S, Hoffman E, Tanswell P, Bette P, Amelsberg A, Rettig W: A phase I dose-escalation study of BIBH1 in patients with advanced or metastatic fibroblast activation protein positive cancer. *Proc AM Soc Clin Oncol* 20: 258a, (2001).

Stemmer et al. Single-step assembly of a gene and entire plasmid from large numbers of oligodeoxyribonucleotides, *Gene* 164(1): 49-53 (1995).

Suzawa et al., *Bioorg. Med. Chem.,* 8, 2175-84 (2000).

Takeya M et al. *Lab Invest* 1995, 72:679-688.

Tanswell P, Garin-Chesa P, Rettig W J, Welt S, Divgi C R, Casper E S, Finn R D, Larson S M, Old L J, Scott A M: Population pharmocokinetics of antifibroblast activation protein monoclonal antibody F19 in cancer patients. *Br. J. Clin. Pharmacol* 51: 177-180, (2001).

Urlaub et al., *Cell* 33: 405-412 (1983).

Welt S, Divgi C R, Scott A M, Garin-Chesa P, Finn R D, Graham M, Carswell E A, Cohen A, Larson S M, Old L J, Rettig W J: Antibody targeting in metastatic colon cancer: A phase I study of monoclonal antibody F19 against a cell-surface protein of reactive tumour stromal fibroblasts. *J. Clin. Oncology* 12: 1193-1203, (1994).

Worrell et al., *Anti-Cancer Drug Design* 1: 179-184 (1986).

Ye et al., Gene synthesis and expression in *E. coli* for pump, a human matrix metalloproteinase. *Biochem Biophys Res Commun* 186(1):143-9 (1992).

Yoshitake et al., *Eur. J. Biochem.,* 101, 395-399 (1979).

The invention claimed is:

1. An isolated anti-FAP-α antibody molecule, or a fragment thereof, selected from
  a. a murine monoclonal antibody, defined by
    i. a variable heavy chain comprising the region from aa 20 to 136 of sequence (SEQ ID NO: 1);
    ii. a variable light chain comprising the region from aa 23 to 129 of sequence (SEQ ID NO:2) and
    iii. the IgG2a kappa subclass; or a fragment thereof;
  b. a chimeric antibody derived from the murine monoclonal antibody defined in a);
  c. a humanized antibody, derived from the murine monoclonal antibody defined in a).

2. The isolated antibody molecule of claim 1, wherein said chimeric antibody b) is defined by
  i. a variable heavy chain comprising the region from aa 20 to 136 of sequence (SEQ ID NO: 1);
  ii. a variable light chain comprising the region from aa 23 to 129 of sequence (SEQ ID NO:2) and
  iii. constant heavy and light chains that are of human origin.

3. The isolated antibody molecule of claim 2, wherein said chimeric antibody has the heavy variable chain region comprising the region from aa 20 to 136 (SEQ ID NO:1) fused to the human heavy chain constant region (SEQ ID NO:3) and the light chain variable region comprising the region from aa 23 to 129 of sequence (SEQ ID NO:2) fused to the human light chain constant region (SEQ ID NO:4).

4. The isolated antibody molecule of claim 1, wherein said humanized antibody c) is defined by
  i. CDRs contained within the variable heavy chain that comprises the region from aa 20 to 136 of sequence (SEQ ID NO:1) and by
  ii. CDRs contained within the variable light chain that comprises the region from aa 23 to 129 of sequence (SEQ ID NO:2)
  iii. frameworks supporting said CDRs that are from a human antibody,
  iv. constant heavy and light chains that are from a human antibody.

5. An isolated antibody molecule of claim 1 which reacts both with murine and human FAP-α.

6. The isolated antibody molecule of claim 1 which recognizes an epitope within the FAP sequence that overlaps with the epitope recognized by the murine monoclonal antibody defined in claim 1 a).

7. The isolated antibody molecule of claim 6 which is a humanized antibody.

8. An immunoconjugate of formula $$A(LB)_n \qquad \text{(Formula (I))}$$

wherein
A is an anti-FAP-α antibody, or a fragment thereof, as defined in claim 1;
L is a linker moiety;
B a cytotoxic agent; and
n is a decimal number with n=1 to 10.

9. The immunoconjugate of claim 8 wherein said linker moiety has a chemical bond capable of being cleaved inside a cell.

10. The immunoconjugate of claim 8, wherein said cytotoxic agent B is a maytansinoid.

11. The immunoconjugate of claim 10, wherein the maytansinoid is DM1.

12. The immunoconjugate of claim 10, wherein the maytansinoid is DM4.

13. The immunoconjugate of claim 8, wherein the linker is selected from
- N-succinimidyl 3-(2-pyridyldithio)propionate (SPDP), N-succinimidyl 4-(2-pyridyldithio)pentanoate (SPP), N-succinimidyl 4-(N-maleimidomethyl)cyclohexane-1-carboxylate (SMCC).

14. Method of producing of an immunoconjugate of claim 8, said methods comprising the steps:
- (a) introducing one or more free or protected thiol groups into an antibody molecule or a fragment thereof, selected from
  - i. a murine monoclonal antibody, defined by
    - a). a variable heavy chain comprising the region from aa 20 to 136 of sequence (SEQ ID NO: 1);
    - b). a variable light chain comprising the region from aa 23 to 129 of sequence (SEQ ID NO:2) and
    - c). the IgG2a kappa subclass;
    - or a fragment thereof;
  - ii. a chimeric antibody derived from the murine monoclonal antibody defined in a);
  - iii. a humanized antibody derived from the murine monoclonal antibody defined in a);
- (b) reacting the antibody molecule obtained in step (a) with a maytansinoid;
- (c) recovering the resulting antibody maytansinoid conjugate.

15. A pharmaceutical composition comprising an immunoconjugate of claim 10 and a pharmaceutically acceptable carrier, diluent, or excipient.

* * * * *

UNITED STATES PATENT AND TRADEMARK OFFICE
CERTIFICATE OF CORRECTION

PATENT NO. : 8,568,727 B2 Page 1 of 1
APPLICATION NO. : 12/159070
DATED : October 29, 2013
INVENTOR(S) : Adolf et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 760 days.

Signed and Sealed this
Twenty-third Day of May, 2017

Michelle K. Lee
*Director of the United States Patent and Trademark Office*

SEQUENCE LISTING

<160> NUMBER OF SEQ ID NOS: 8

<210> SEQ ID NO 1
<211> LENGTH: 149
<212> TYPE: PRT
<213> ORGANISM: Mus musculus

<400> SEQUENCE: 1

Met Gly Trp Ser Gly Val Phe Ile Phe Ile Leu Ser Gly Thr Ala Gly
1               5                   10                  15

Val Gln Ser Gln Val Gln Leu Gln Gln Ser Gly Ala Glu Leu Ala Arg
            20                  25                  30

Pro Gly Ala Ser Val Asn Leu Ser Cys Lys Ala Ser Gly Tyr Thr Phe
        35                  40                  45

Thr Asn Asn Gly Ile Asn Trp Leu Lys Gln Arg Thr Gly Gln Gly Leu
    50                  55                  60

Glu Trp Ile Gly Glu Ile Tyr Pro Arg Ser Thr Asn Thr Leu Tyr Asn
65                  70                  75                  80

Glu Lys Phe Lys Gly Lys Ala Thr Leu Thr Ala Asp Arg Ser Ser Asn
                85                  90                  95

Thr Ala Tyr Met Glu Leu Arg Ser Leu Thr Ser Glu Asp Ser Ala Val
            100                 105                 110

Tyr Phe Cys Ala Arg Thr Leu Thr Ala Pro Phe Ala Phe Trp Gly Gln
        115                 120                 125

Gly Thr Leu Val Thr Val Ser Ala Ala Lys Thr Thr Ala Pro Ser Val
    130                 135                 140

Tyr Pro Leu Ala Pro
145

<210> SEQ ID NO 2
<211> LENGTH: 137
<212> TYPE: PRT
<213> ORGANISM: Mus musculus

<400> SEQUENCE: 2

Met Asp Phe Gln Val Gln Ile Phe Ser Phe Leu Leu Ile Ser Ala Ser
1               5                   10                  15

Val Ile Ile Ser Arg Gly Gln Ile Val Leu Thr Gln Ser Pro Ala Ile
            20                  25                  30

Met Ser Ala Ser Pro Gly Glu Lys Val Thr Met Thr Cys Ser Ala Ser
        35                  40                  45

Ser Gly Val Asn Phe Met His Trp Tyr Gln Gln Lys Ser Gly Thr Ser
    50                  55                  60

Pro Lys Arg Trp Ile Phe Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Trp
            100                 105                 110

Ser Phe Asn Pro Pro Thr Phe Gly Gly Gly Thr Lys Leu Glu Ile Lys
        115                 120                 125

Arg Ala Asp Ala Ala Pro Thr Val Ser
    130                 135

<210> SEQ ID NO 3
<211> LENGTH: 466

```
<212> TYPE: PRT
<213> ORGANISM: Artificial sequence
<220> FEATURE:
<223> OTHER INFORMATION: Chimeric protein comprising fusion of murine
      and human sequences

<400> SEQUENCE: 3
```

| | | | | | | | | | | | | | | |
|---|---|---|---|---|---|---|---|---|---|---|---|---|---|---|
| Met | Gly | Trp | Ser | Gly | Val | Phe | Ile | Phe | Ile | Leu | Ser | Gly | Thr | Ala | Gly |
| 1 | | | | 5 | | | | | 10 | | | | | 15 |
| Val | Gln | Ser | Gln | Val | Gln | Leu | Gln | Gln | Ser | Gly | Ala | Glu | Leu | Ala | Arg |
| | | | 20 | | | | | 25 | | | | | 30 | |
| Pro | Gly | Ala | Ser | Val | Asn | Leu | Ser | Cys | Lys | Ala | Ser | Gly | Tyr | Thr | Phe |
| | | | 35 | | | | | 40 | | | | | 45 | |
| Thr | Asn | Asn | Gly | Ile | Asn | Trp | Leu | Lys | Gln | Arg | Thr | Gly | Gln | Gly | Leu |
| | 50 | | | | | 55 | | | | | 60 | | | |
| Glu | Trp | Ile | Gly | Glu | Ile | Tyr | Pro | Arg | Ser | Thr | Asn | Thr | Leu | Tyr | Asn |
| 65 | | | | | 70 | | | | | 75 | | | | | 80 |
| Glu | Lys | Phe | Lys | Gly | Lys | Ala | Thr | Leu | Thr | Ala | Asp | Arg | Ser | Ser | Asn |
| | | | | 85 | | | | | 90 | | | | | 95 | |
| Thr | Ala | Tyr | Met | Glu | Leu | Arg | Ser | Leu | Thr | Ser | Glu | Asp | Ser | Ala | Val |
| | | | 100 | | | | | 105 | | | | | 110 | | |
| Tyr | Phe | Cys | Ala | Arg | Thr | Leu | Thr | Ala | Pro | Phe | Ala | Phe | Trp | Gly | Gln |
| | | 115 | | | | | 120 | | | | | 125 | | | |
| Gly | Thr | Leu | Val | Thr | Val | Ser | Ala | Ala | Ser | Thr | Lys | Gly | Pro | Ser | Val |
| | 130 | | | | | 135 | | | | | 140 | | | | |
| Phe | Pro | Leu | Ala | Pro | Ser | Ser | Lys | Ser | Thr | Ser | Gly | Gly | Thr | Ala | Ala |
| 145 | | | | | 150 | | | | | 155 | | | | | 160 |
| Leu | Gly | Cys | Leu | Val | Lys | Asp | Tyr | Phe | Pro | Glu | Pro | Val | Thr | Val | Ser |
| | | | | 165 | | | | | 170 | | | | | 175 | |
| Trp | Asn | Ser | Gly | Ala | Leu | Thr | Ser | Gly | Val | His | Thr | Phe | Pro | Ala | Val |
| | | | 180 | | | | | 185 | | | | | 190 | | |
| Leu | Gln | Ser | Ser | Gly | Leu | Tyr | Ser | Leu | Ser | Ser | Val | Val | Thr | Val | Pro |
| | | 195 | | | | | 200 | | | | | 205 | | | |
| Ser | Ser | Ser | Leu | Gly | Thr | Gln | Thr | Tyr | Ile | Cys | Asn | Val | Asn | His | Lys |
| | 210 | | | | | 215 | | | | | 220 | | | | |
| Pro | Ser | Asn | Thr | Lys | Val | Asp | Lys | Lys | Val | Glu | Pro | Lys | Ser | Cys | Asp |
| 225 | | | | | 230 | | | | | 235 | | | | | 240 |
| Lys | Thr | His | Thr | Cys | Pro | Pro | Cys | Pro | Ala | Pro | Glu | Leu | Leu | Gly | Gly |
| | | | | 245 | | | | | 250 | | | | | 255 | |
| Pro | Ser | Val | Phe | Leu | Phe | Pro | Pro | Lys | Pro | Lys | Asp | Thr | Leu | Met | Ile |
| | | | 260 | | | | | 265 | | | | | 270 | | |
| Ser | Arg | Thr | Pro | Glu | Val | Thr | Cys | Val | Val | Val | Asp | Val | Ser | His | Glu |
| | | 275 | | | | | 280 | | | | | 285 | | | |
| Asp | Pro | Glu | Val | Lys | Phe | Asn | Trp | Tyr | Val | Asp | Gly | Val | Glu | Val | His |
| | 290 | | | | | 295 | | | | | 300 | | | | |
| Asn | Ala | Lys | Thr | Lys | Pro | Arg | Glu | Glu | Gln | Tyr | Asn | Ser | Thr | Tyr | Arg |
| 305 | | | | | 310 | | | | | 315 | | | | | 320 |
| Val | Val | Ser | Val | Leu | Thr | Val | Leu | His | Gln | Asp | Trp | Leu | Asn | Gly | Lys |
| | | | | 325 | | | | | 330 | | | | | 335 | |
| Glu | Tyr | Lys | Cys | Lys | Val | Ser | Asn | Lys | Ala | Leu | Pro | Ala | Pro | Ile | Glu |
| | | | 340 | | | | | 345 | | | | | 350 | | |
| Lys | Thr | Ile | Ser | Lys | Ala | Lys | Gly | Gln | Pro | Arg | Glu | Pro | Gln | Val | Tyr |
| | | 355 | | | | | 360 | | | | | 365 | | | |
| Thr | Leu | Pro | Pro | Ser | Arg | Asp | Glu | Leu | Thr | Lys | Asn | Gln | Val | Ser | Leu |
| | 370 | | | | | 375 | | | | | 380 | | | | |

```
Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
    450                 455                 460

Gly Lys
465

<210> SEQ ID NO 4
<211> LENGTH: 235
<212> TYPE: PRT
<213> ORGANISM: Artificial sequence
<220> FEATURE:
<223> OTHER INFORMATION: Chimeric protein comprising fusion of murine
      and human sequences

<400> SEQUENCE: 4

Met Asp Phe Gln Val Gln Ile Phe Ser Phe Leu Leu Ile Ser Ala Ser
1               5                   10                  15

Val Ile Ile Ser Arg Gly Gln Ile Val Leu Thr Gln Ser Pro Ala Ile
                20                  25                  30

Met Ser Ala Ser Pro Gly Glu Lys Val Thr Met Thr Cys Ser Ala Ser
            35                  40                  45

Ser Gly Val Asn Phe Met His Trp Tyr Gln Gln Lys Ser Gly Thr Ser
50                  55                  60

Pro Lys Arg Trp Ile Phe Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Trp
            100                 105                 110

Ser Phe Asn Pro Pro Thr Phe Gly Gly Gly Thr Lys Leu Glu Ile Lys
            115                 120                 125

Arg Thr Val Ala Ala Pro Ser Val Phe Ile Phe Pro Pro Ser Asp Glu
            130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
            195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 5
<211> LENGTH: 931
<212> TYPE: PRT
<213> ORGANISM: Mus musculus
```

-continued

<400> SEQUENCE: 5

```
Met Asp Ile Cys Arg Ile Arg Ala Arg Met Ala Ser Pro Leu Thr Arg
1               5                   10                  15

Phe Leu Ser Leu Asn Leu Leu Leu Gly Glu Ser Ile Ile Leu Gly
            20                  25                  30

Ser Gly Glu Ala Lys Pro Gln Ala Pro Glu Leu Arg Ile Phe Pro Lys
            35                  40                  45

Lys Met Asp Ala Glu Leu Gly Gln Lys Val Asp Leu Val Cys Glu Val
50                  55                  60

Leu Gly Ser Val Ser Gln Gly Cys Ser Trp Leu Phe Gln Asn Ser Ser
65                  70                  75                  80

Ser Lys Leu Pro Gln Pro Thr Phe Val Val Tyr Met Ala Ser Ser His
            85                  90                  95

Asn Lys Ile Thr Trp Asp Glu Lys Leu Asn Ser Ser Lys Leu Phe Ser
            100                 105                 110

Ala Met Arg Asp Thr Asn Asn Lys Tyr Val Leu Thr Leu Asn Lys Phe
            115                 120                 125

Ser Lys Glu Asn Glu Gly Tyr Tyr Phe Cys Ser Val Ile Ser Asn Ser
            130                 135                 140

Val Met Tyr Phe Ser Ser Val Val Pro Val Leu Gln Lys Val Asn Ser
145                 150                 155                 160

Thr Thr Thr Lys Pro Val Leu Arg Thr Pro Ser Pro Val His Pro Thr
            165                 170                 175

Gly Thr Ser Gln Pro Gln Arg Pro Glu Asp Cys Arg Pro Arg Gly Ser
            180                 185                 190

Ile Glu Gly Arg Arg Pro Ser Arg Val Tyr Lys Pro Glu Gly Asn Thr
            195                 200                 205

Lys Arg Ala Leu Thr Leu Lys Asp Ile Leu Asn Gly Thr Phe Ser Tyr
210                 215                 220

Lys Thr Tyr Phe Pro Asn Trp Ile Ser Glu Gln Glu Tyr Leu His Gln
225                 230                 235                 240

Ser Glu Asp Asp Asn Ile Val Phe Tyr Asn Ile Glu Thr Arg Glu Ser
            245                 250                 255

Tyr Ile Ile Leu Ser Asn Ser Thr Met Lys Ser Val Asn Ala Thr Asp
            260                 265                 270

Tyr Gly Leu Ser Pro Asp Arg Gln Phe Val Tyr Leu Glu Ser Asp Tyr
            275                 280                 285

Ser Lys Leu Trp Arg Tyr Ser Tyr Thr Ala Thr Tyr Tyr Ile Tyr Asp
            290                 295                 300

Leu Gln Asn Gly Glu Phe Val Arg Gly Tyr Glu Leu Pro Arg Pro Ile
305                 310                 315                 320

Gln Tyr Leu Cys Trp Ser Pro Val Gly Ser Lys Leu Ala Tyr Val Tyr
            325                 330                 335

Gln Asn Asn Ile Tyr Leu Lys Gln Arg Pro Gly Asp Pro Pro Phe Gln
            340                 345                 350

Ile Thr Tyr Thr Gly Arg Glu Asn Arg Ile Phe Asn Gly Ile Pro Asp
            355                 360                 365

Trp Val Tyr Glu Glu Glu Met Leu Ala Thr Lys Tyr Ala Leu Trp Trp
            370                 375                 380

Ser Pro Asp Gly Lys Phe Leu Ala Tyr Val Glu Phe Asn Asp Ser Asp
385                 390                 395                 400

Ile Pro Ile Ile Ala Tyr Ser Tyr Tyr Gly Asp Gly Gln Tyr Pro Arg
            405                 410                 415
```

-continued

```
Thr Ile Asn Ile Pro Tyr Pro Lys Ala Gly Lys Asn Pro Val Val
            420                 425                 430

Arg Val Phe Ile Val Asp Thr Thr Tyr Pro His His Val Gly Pro Met
        435                 440                 445

Glu Val Pro Val Pro Glu Met Ile Ala Ser Ser Asp Tyr Tyr Phe Ser
    450                 455                 460

Trp Leu Thr Trp Val Ser Ser Glu Arg Val Cys Leu Gln Trp Leu Lys
465                 470                 475                 480

Arg Val Gln Asn Val Ser Val Leu Ser Ile Cys Asp Phe Arg Glu Asp
                485                 490                 495

Trp His Ala Trp Glu Cys Pro Lys Asn Gln Glu His Val Glu Glu Ser
            500                 505                 510

Arg Thr Gly Trp Ala Gly Gly Phe Phe Val Ser Thr Pro Ala Phe Ser
        515                 520                 525

Gln Asp Ala Thr Ser Tyr Tyr Lys Ile Phe Ser Asp Lys Asp Gly Tyr
    530                 535                 540

Lys His Ile His Tyr Ile Lys Asp Thr Val Glu Asn Ala Ile Gln Ile
545                 550                 555                 560

Thr Ser Gly Lys Trp Glu Ala Ile Tyr Ile Phe Arg Val Thr Gln Asp
                565                 570                 575

Ser Leu Phe Tyr Ser Ser Asn Glu Phe Glu Gly Tyr Pro Gly Arg Arg
            580                 585                 590

Asn Ile Tyr Arg Ile Ser Ile Gly Asn Ser Pro Pro Ser Lys Lys Cys
        595                 600                 605

Val Thr Cys His Leu Arg Lys Arg Cys Gln Tyr Tyr Thr Ala Ser
    610                 615                 620

Phe Ser Tyr Lys Ala Lys Tyr Ala Leu Val Cys Tyr Gly Pro Gly
625                 630                 635                 640

Leu Pro Ile Ser Thr Leu His Asp Gly Arg Thr Asp Gln Glu Ile Gln
                645                 650                 655

Val Leu Glu Glu Asn Lys Glu Leu Glu Asn Ser Leu Arg Asn Ile Gln
            660                 665                 670

Leu Pro Lys Val Glu Ile Lys Lys Leu Lys Asp Gly Gly Leu Thr Phe
        675                 680                 685

Trp Tyr Lys Met Ile Leu Pro Pro Gln Phe Asp Arg Ser Lys Lys Tyr
    690                 695                 700

Pro Leu Leu Ile Gln Val Tyr Gly Gly Pro Cys Ser Gln Ser Val Lys
705                 710                 715                 720

Ser Val Phe Ala Val Asn Trp Ile Thr Tyr Leu Ala Ser Lys Glu Gly
                725                 730                 735

Ile Val Ile Ala Leu Val Asp Gly Arg Gly Thr Ala Phe Gln Gly Asp
            740                 745                 750

Lys Phe Leu His Ala Val Tyr Arg Lys Leu Gly Val Tyr Glu Val Glu
        755                 760                 765

Asp Gln Leu Thr Ala Val Arg Lys Phe Ile Glu Met Gly Phe Ile Asp
    770                 775                 780

Glu Glu Arg Ile Ala Ile Trp Gly Trp Ser Tyr Gly Gly Tyr Val Ser
785                 790                 795                 800

Ser Leu Ala Leu Ala Ser Gly Thr Gly Leu Phe Lys Cys Gly Ile Ala
                805                 810                 815

Val Ala Pro Val Ser Ser Trp Glu Tyr Tyr Ala Ser Ile Tyr Ser Glu
            820                 825                 830

Arg Phe Met Gly Leu Pro Thr Lys Asp Asp Asn Leu Glu His Tyr Lys
        835                 840                 845
```

```
Asn Ser Thr Val Met Ala Arg Ala Glu Tyr Phe Arg Asn Val Asp Tyr
        850                 855                 860

Leu Leu Ile His Gly Thr Ala Asp Asp Asn Val His Phe Gln Asn Ser
865                 870                 875                 880

Ala Gln Ile Ala Lys Ala Leu Val Asn Ala Gln Val Asp Phe Gln Ala
                885                 890                 895

Met Trp Tyr Ser Asp Gln Asn His Gly Ile Ser Ser Gly Arg Ser Gln
                900                 905                 910

Asn His Leu Tyr Thr His Met Thr His Phe Leu Lys Gln Cys Phe Ser
            915                 920                 925

Leu Ser Asp
    930

<210> SEQ ID NO 6
<211> LENGTH: 117
<212> TYPE: PRT
<213> ORGANISM: Artificial
<220> FEATURE:
<223> OTHER INFORMATION: Humanized mouse sequence

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Asn
                20                  25                  30

Gly Ile Asn Trp Leu Arg Gln Ala Pro Gly Gln Gly Leu Glu Trp Met
            35                  40                  45

Gly Glu Ile Tyr Pro Arg Ser Thr Asn Thr Leu Tyr Ala Gln Lys Phe
    50                  55                  60

Gln Gly Arg Val Thr Ile Thr Ala Asp Arg Ser Ser Asn Thr Ala Tyr
65                  70                  75                  80

Met Glu Leu Ser Ser Leu Arg Ser Glu Asp Thr Ala Val Tyr Phe Cys
                85                  90                  95

Ala Arg Thr Leu Thr Ala Pro Phe Ala Phe Trp Gly Gln Gly Thr Leu
                100                 105                 110

Val Thr Val Ser Ser
        115

<210> SEQ ID NO 7
<211> LENGTH: 107
<212> TYPE: PRT
<213> ORGANISM: Artificial
<220> FEATURE:
<223> OTHER INFORMATION: Humanized mouse sequence

<400> SEQUENCE: 7

Gln Ile Val Leu Thr Gln Ser Pro Ala Thr Leu Ser Leu Ser Pro Gly
1               5                   10                  15

Glu Arg Ala Thr Leu Ser Cys Ser Ala Ser Ser Gly Val Asn Phe Met
                20                  25                  30

His Trp Tyr Gln Gln Lys Pro Gly Gln Ala Pro Arg Arg Leu Ile Phe
            35                  40                  45

Asp Thr Ser Lys Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Phe Asn Pro Pro Thr
                85                  90                  95
```

```
Phe Gly Gln Gly Thr Lys Val Glu Ile Lys Arg
                100                 105

<210> SEQ ID NO 8
<211> LENGTH: 107
<212> TYPE: PRT
<213> ORGANISM: Artificial
<220> FEATURE:
<223> OTHER INFORMATION: Humanized mouse sequence

<400> SEQUENCE: 8

Gln Ile Val Leu Thr Gln Ser Pro Ala Thr Leu Ser Leu Ser Pro Gly
1               5                   10                  15

Glu Arg Ala Thr Leu Ser Cys Ser Ala Ser Ser Gly Val Asn Phe Met
            20                  25                  30

His Trp Tyr Gln Gln Lys Pro Gly Gln Ala Pro Lys Arg Leu Ile Phe
        35                  40                  45

Asp Thr Ser Lys Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Phe Asn Pro Pro Thr
                85                  90                  95

Phe Gly Gln Gly Thr Lys Val Glu Ile Lys Arg
                100                 105
```